(12) United States Patent
Cai et al.

(10) Patent No.: US 7,928,136 B2
(45) Date of Patent: Apr. 19, 2011

(54) SUBSTITUTED 2-INDOLINONE AS PTK INHIBITORS CONTAINING A ZINC BINDING MOIETY

(75) Inventors: Xiong Cai, Belmont, MA (US); Changgeng Qian, Wayland, MA (US); Stephen Gould, San Carlos, CA (US)

(73) Assignee: Curis, Inc., Lexington, MA (US)

( * ) Notice: Subject to any disclaimer, the term of this patent is extended or adjusted under 35 U.S.C. 154(b) by 331 days.

(21) Appl. No.: 11/852,419

(22) Filed: Sep. 10, 2007

(65) Prior Publication Data

US 2008/0125478 A1    May 29, 2008

Related U.S. Application Data

(60) Provisional application No. 60/843,634, filed on Sep. 11, 2006, provisional application No. 60/895,880, filed on Mar. 20, 2007.

(51) Int. Cl.
*A61K 31/404* (2006.01)
*C07D 209/04* (2006.01)

(52) U.S. Cl. .......................... 514/414; 548/465

(58) Field of Classification Search .................. 514/414; 548/465
See application file for complete search history.

(56) References Cited

U.S. PATENT DOCUMENTS

| 6,087,367 A | 7/2000 | Breslow et al. |
| 6,653,308 B2 | 11/2003 | Guan et al. |
| 6,777,217 B1 | 8/2004 | Schreiber et al. |
| 7,250,514 B1 | 7/2007 | Xiao |
| 2008/0221132 A1 | 9/2008 | Cai et al. |

FOREIGN PATENT DOCUMENTS

| WO | 2002/068396 A1 | 9/2002 |
| WO | 2003/015608 A2 | 2/2003 |
| WO | 2003057690 A1 | 7/2003 |
| WO | 2005/053614 A2 | 6/2005 |
| WO | 2005/053686 A1 | 6/2005 |
| WO | 2005/058309 A1 | 6/2005 |
| WO | 2006/082428 A2 | 8/2006 |
| WO | 2007/131364 A1 | 11/2007 |
| WO | 2008/055068 A2 | 5/2008 |

OTHER PUBLICATIONS

Vippagunta et al., Crystalline solids, 2001, Advanced Drug Delivery Reviews, 48, pp. 3 and 18.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Butler, Lisa M., et al., "Suberoylanilide Hydroxamic Acid, an Inhibitor of Histone Deacetylase, Suppresses the Growth of Prostate Cancer Cells in Vitro and in Vivo," Cancer Research, 60: 5165-5170 (2000).

* cited by examiner

*Primary Examiner* — Kamal A Saeed
*Assistant Examiner* — Kristin Bianchi
(74) *Attorney, Agent, or Firm* — Elmore Patent Law Group, P.C.; Edgar W. Harlan; Carolyn S. Elmore

(57) ABSTRACT

The present invention relates to substituted 2-indolinone containing zinc-binding moiety based derivatives that have enhanced or unique properties as inhibitors of protein tyrosine kinase (PTK) receptors and their use in the treatment of PTK related diseases and disorders such as cancer. The said derivatives may further act as HDAC inhibitors.

11 Claims, No Drawings

SUBSTITUTED 2-INDOLINONE AS PTK INHIBITORS CONTAINING A ZINC BINDING MOIETY

RELATED APPLICATIONS

This application claims the benefit of U.S. Provisional Application No. 60/843,634, filed on Sep. 11, 2006 and U.S. Provisional Application No. 60/895,880, filed on Mar. 20, 2007. The entire teachings of the above applications are incorporated herein by reference.

BACKGROUND OF THE INVENTION

Protein kinases (PK) are enzymes that catalyze the phosphorylation of hydroxyl groups of tyrosine, serine, and threonine residues of proteins. Many aspects of cell life such as cell growth, differentiation, proliferation, cell cycle and survival, depend on protein kinase activities. Furthermore, abnormal protein kinase activity has been related to a host of disorders such as cancer and inflammation. Therefore, there is a great deal of effort directed to identifying ways to modulate protein kinase activities.

Receptor tyrosine kinases ("RTKs") comprise a large family of transmembrane receptors with diverse biological activity. At present, at least nineteen distinct subfamilies of RTKs have been identified. An example of these is the subfamily platelet derived growth factor receptor ("PDGFR"), which includes PDGFRα, PDGFRβ, CSFIR, c-kit and c-fms. These receptors consist of glycosylated extracellular domains composed of variable numbers of immunoglobin-like loops and an intracellular domain wherein the tyrosine kinase domain is interrupted by unrelated amino acid sequences. Another group which, because of its similarity to the PDGFR subfamily, is sometimes subsumed into the later group is the fetus liver kinase ("flk") receptor subfamily. This group is believed to be made up of kinase insert domain-receptor fetal liver kinase-1 (KDR/FLK-1, VEGF-R2), flk-1R, flk-4 and fins-like tyrosine kinase 1 (flt-1). A further member of the tyrosine kinase growth factor receptor family is the vascular endothelial growth factor (VEGF") receptor subgroup. VEGF is a dimeric glycoprotein similar to PDGF but has different biological functions and target cell specificity in vivo. In particular, VEGF is presently thought to play an essential role is vasculogenesis and angiogenesis. A more complete listing of the known RTK subfamilies is described in Plowman et al., *DN&P*, 1994, 7(6):334-339.

The dramatic clinical success of the tyrosine kinase inhibitor. Gleevec (ABL tyrosine kinase), in the treatment of Chronic Myeloid Leukemia (CML) has spurred a flurry of activity to develop inhibitors of the entire kinome. Despite the early success with Gleevec, it has become clear that selectively targeting individual kinases can lead to the development of drug resistant tumors. Cells that have developed mutations within the drug/kinase binding pocket display a growth advantage in the presence of drug eventually leading to disease progression.

To help reduce the chance of developing such drug resistant tumors and to increase the overall response rates observed, pharmaceutical companies have now started to develop broadly acting kinase inhibitors (Atkins, M, et al., *Nat Rev Drug Discov* 5(4), 2006, 279-280; Kling, J., *Nat Biotechnol* 24(8), 2006, 871-2; Frantz, S., *Nature*, 2006, 942-943; Garber, K., *Nat Biotechnol*, 2006, 24(2) 127-130). Pyrrole substituted 2-indolinone derivatives as receptor tyrosine kinase inhibitors useful in the treatment of conditions responsive to receptor tyrosine kinase inhibitors, for example, proliferative disorders such as cancer, are disclosed in WO 96/40116, WO 99/61422, WO 01/60814, WO 01/42243, and WO 02/055517. Sutent® (suntunib), currently marketed by Pfizer, is an example of the 2-indolinone protein tyrosine kinase (PTK) class targeting PDGF, VEGFR, KIT, Flt3, CSF-1R, and RET and has shown positive clinical activity in a number of types of solid tumors including renal cell carcinoma (RCC) and gastrointestinal stromal tumor (GIST).

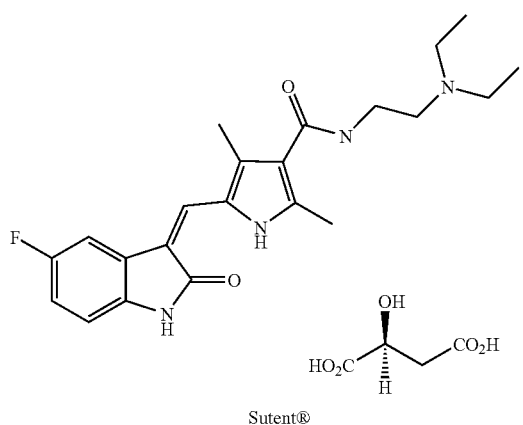

Sutent®

Furthermore, elucidation of the complex and multifactorial nature of various diseases that involve multiple pathogenic pathways and numerous molecular components suggests that multi-targeted therapies may be advantageous over monotherapies. Recent combination therapies with two or more agents for many such diseases in the areas of oncology, infectious disease, cardiovascular disease and other complex pathologies demonstrate that this combinatorial approach may provide advantages with respect to overcoming drug resistance, reduced toxicity and, in some circumstances, a synergistic therapeutic effect compared to the individual components.

Certain cancers have been effectively treated with such a combinatorial approach; however, treatment regimes using a cocktail of cytotoxic drugs often are limited by dose limiting toxicities and drug-drug interactions. More recent advances with molecularly targeted drugs have provided new approaches to combination treatment for cancer, allowing multiple targeted agents to be used simultaneously, or combining these new therapies with standard chemotherapeutics or radiation to improve outcome without reaching dose limiting toxicities. However, the ability to use such combinations currently is limited to drugs that show compatible pharmacologic and pharmacodynamic properties. In addition, the regulatory requirements to demonstrate safety and efficacy of combination therapies can be more costly and lengthy than corresponding single agent trials. Once approved, combination strategies may also be associated with increased costs to patients, as well as decreased patient compliance owing to the more intricate dosing paradigms required.

In the field of protein and polypeptide-based therapeutics it has become a commonplace to prepare conjugates or fusion proteins that contain most or all of the amino acid sequences of two different proteins/polypeptides and that retain the individual binding activities of the separate proteins/polypeptides. This approach is made possible by independent folding of the component protein domains and the large size of the conjugates that permits the components to bind their cellular targets in an essentially independent manner. Such an approach is not, however, generally feasible in the case of small molecule therapeutics, where even minor structural modifications can lead to major changes in target binding and/or the pharmacokinetic/pharmacodynamic properties of the resulting molecule.

The use of histone deacetylases (HDAC) in combination with other targeted agents has been shown to produce synergistic effects. Histone acetylation is a reversible modification, with deacetylation being catalyzed by a family of enzymes termed HDAC's. HDAC's are represented by X genes in humans and are divided into four distinct classes (*J Mol Biol*, 2004, 338:1, 17-31). In mammalians class I HDAC's (HDAC1-3, and HDAC8) are related to yeast RPD3 HDAC, class 2 (HDAC4-7, HDAC9 and HDAC10) related to yeast HDA1, class 4 (HDAC11), and class 3 (a distinct class encompassing the sirtuins which are related to yeast Sir2).

Csordas, *Biochem. J.,* 1990, 286: 23-38 teaches that histones are subject to post-translational acetylation of the, ε-amino groups of N-terminal lysine residues, a reaction that is catalyzed by histone acetyl transferase (HAT1). Acetylation neutralizes the positive charge of the lysine side chain, and is thought to impact chromatin structure. Indeed, access of transcription factors to chromatin templates is enhanced by histone hyperacetylation, and enrichment in underacetylated histone H4 has been found in transcriptionally silent regions of the genome (Taunton et al., *Science,* 1996, 272:408-411). In the case of tumor suppressor genes, transcriptional silencing due to histone modification can lead to oncogenic transformation and cancer.

Several classes of HDAC inhibitors currently are being evaluated by clinical investigators. The first FDA approved HDAC inhibitor is Suberoylanilide hydroxamic acid (SAHA, Zolinza®) for the treatment of cutaneous T-cell lymphoma (CTCL). Other HDAC inhibitors include hydroxamic acid derivatives, PXD 101 and LAQ824, are currently in the clinical development. In the benzamide class of HDAC inhibitors, MS-275, MGCD0103 and CI-994 have reached clinical trials. Mourne et al. (Abstract #4725, AACR 2005), demonstrate that thiophenyl modification of benzamides significantly enhance HDAC inhibitory activity against HDAC 1.

Recent advances suggest that HDAC inhibitors in combination with other targeted agents may provide advantageous results in the treatment of cancer. For example, co-treatment with SAHA significantly increased EGFR2 antibody trastuzumab-induced apoptosis of BT-474 and SKBR-3 cells and induced synergistic cytotoxic effects against the breast cancer cells (Bali, *Clin. Cancer Res.,* 2005, 11, 3392). HDAC inhibitors, such as SAHA, have demonstrated synergistic antiproliferative and apoptotic effects when used in combination with gefitinib in head and neck cancer cell lines, including lines that are resistant to gefitinib monotherapy (Bruzzese et al., Proc. AACR, 2004). Pretreating gefitinib resistant cell lines with the HDAC inhibitor, MS-275, led to a growth-inhibitory and apoptotic effect of gefitinib similar to that seen in gefitinib-sensitive NSCLC cell lines including those harboring EGFR mutations (Witta S. E., et al., *Cancer Res* 66:2, 2006, 944-50). The HDAC inhibitor PXD101 has been shown to act synergistically to inhibit proliferation with the EGFR1 inhibitor Tarceva® (erlotinib) (WO2006082428A2).

Anti-tumor activity observed in PC3 xenografts of the HDAC inhibitor FK228, is dependent upon the repression of angiogenic factors such as VEGF and βFGF (Sasakawa et al., *Biochem. Pharmacol.,* 2003, 66, 897). The HDAC inhibitor NVP-LAQ824 has been shown to inhibit angiogenesis and has a greater anti-tumor effect when used in combination with the vascular endothelial growth factor receptor tyrosine kinase inhibitor PTK787/ZK222584 (Qian et al., *Cancer Res.,* 2004, 64, 66260).

Current therapeutic regimens of the types described above attempt to address the problem of drug resistance by the administration of multiple agents. However, the combined toxicity of multiple agents due to off-target side effects as well as drug-drug interactions often limit the effectiveness of this approach. Moreover, it often is difficult to combine compounds having differing pharmacokinetics into a single dosage form, and the consequent requirement of taking multiple medications at different time intervals leads to problems with patient compliance that can undermine the efficacy of the drug combinations. In addition, the health care costs of combination therapies may be greater than for single molecule therapies. Moreover, it may be more difficult to obtain regulatory approval of a combination therapy since the burden for demonstrating activity/safety of a combination of two agents may be greater than for a single agent. (Dancey J & Chen H, *Nat. Rev. Drug Dis.,* 2006, 5:649). The development of novel agents that target multiple therapeutic targets selected not by virtue of cross reactivity, but through rational design will help improve patient outcome while avoiding these limitations. Thus, enormous efforts are still directed to the development of selective anti-cancer drugs as well as to new and more efficacious combinations of known anti-cancer drugs.

SUMMARY OF THE INVENTION

The present invention relates to substituted 2-indolinone containing zinc-binding moiety based derivatives that have enhanced properties as inhibitors of protein tyrosine kinase (PTK) receptors and their use in the treatment of PTK related diseases and disorders such as cancer. The said derivatives may further act as HDAC inhibitors.

The compounds of the present invention may further act as HDAC or matrix metalloproteinase (MMP) inhibitors by virtue of their ability to bind zinc ions. Surprisingly these compounds are active at multiple therapeutic targets and are effective for treating disease. Moreover, in some cases it has even more surprisingly been found that the compounds have enhanced activity when compared to the activities of combinations of separate molecules individually having the PTK and HDAC activities. In other words, the combination of pharmacophores into a single molecule may provide a synergistic effect as compared to the individual pharmacophores. More specifically, it has been found that it is possible to prepare compounds that simultaneously contain a first portion of the molecule that binds zinc ions and thus permits inhibition of HDAC and/or matrix metalloproteinase (MMP) activity and at least a second portion of the molecule that permits binding to a separate and distinct target thereby permits PTK inhibition and thus provides therapeutic benefit. Preferably, the compounds of the present invention inhibit both PTKs and HDAC activity.

Accordingly, the present invention provides a compound having the general Formula I:

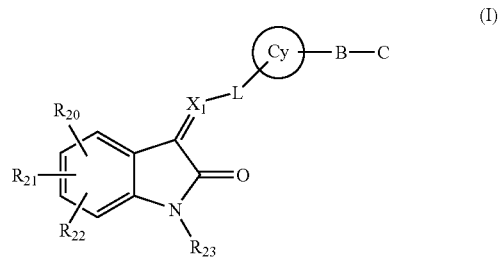

or its geometric isomers, enantiomers, diastereomers, racemates, pharmaceutically acceptable salts, prodrugs and solvates thereof, wherein $X_1$ is N, $CR_4$; where $R_4$ is hydrogen or aliphatic;

L is absent or NH;

Cy is an aryl, substituted aryl, heteroaryl, substituted heteroaryl;

B is a direct bond or straight or branched, substituted or unsubstituted alkylene, substituted or unsubstituted alkenylene, substituted or unsubstituted alkynylene, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, or alkynylhereroaryl, which one or more methylenes can be interrupted or terminated by O, S, S(O), $SO_2$, $N(R_8)$, C(O), substituted or unsubstituted aryl, substituted or unsubstituted heteroaryl, substituted or unsubstituted heterocyclic; where $R_8$ is hydrogen, acyl, aliphatic or substituted aliphatic;

In one embodiment, the linker B is between 1-24 atoms, preferably 4-24 atoms, preferably 4-18 atoms, more preferably 4-12 atoms, and most preferably about 4-10 atoms;

C is selected from:

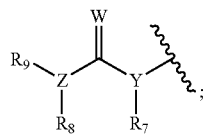
(a)

where W is O or S; Y is absent, N, or CH; Z is N or CH; $R_7$ and $R_9$ are independently hydrogen, OR' or aliphatic, wherein R' is hydrogen, aliphatic, substituted aliphatic or acyl; provided that if $R_7$ and $R_9$ are both present, one of $R_7$ or $R_9$ must be OR' and if Y is absent, $R_9$ must be OR'; and $R_8$ is hydrogen, acyl, aliphatic, or substituted aliphatic;

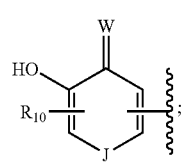
(b)

where W is O or S; J is O, NH or $NCH_3$; and $R_{10}$ is hydrogen or lower alkyl;

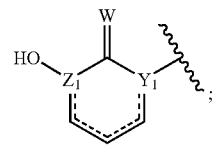
(c)

where W is O or S; $Y_1$ and $Z_1$ are independently N, C or CH; and

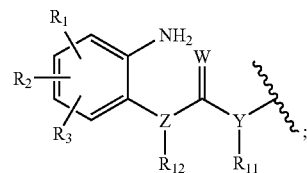
(d)

where Z, Y, and W are as previously defined; $R_{11}$ and $R_{12}$ are independently selected from hydrogen or aliphatic; $R_1$, $R_2$ and $R_3$ are independently selected from hydrogen, hydroxy, amino, halogen, alkoxy, substituted alkoxy, alkylamino, substituted alkylamino, dialkylamino, substituted dialkylamino, substituted or unsubstituted alkylthio, substituted or unsubstituted alkylsulfonyl, $CF_3$, CN, $N_3$, $NO_2$, sulfonyl, acyl, aliphatic, substituted aliphatic, aryl, substituted aryl, heteroaryl, substituted heteroaryl, heterocyclic, and substituted heterocyclic;

$R_{20}$, $R_{21}$, $R_{22}$ are independently selected from $R_1$; and $R_{23}$ is hydrogen, acyl, aliphatic or substituted aliphatic.

DETAILED DESCRIPTION OF THE INVENTION

In a first embodiment of the compounds of the present invention are compounds represented by formula (I) as illustrated above, or its geometric isomers, enantiomers, diastereomers, racemates, pharmaceutically acceptable salts, prodrugs and solvates thereof.

In a second embodiment of the compounds of the present invention are compounds represented by formula (II) as illustrated below, or its geometric isomers, enantiomers, diastereomers, racemates, pharmaceutically acceptable salts, prodrugs and solvates thereof:

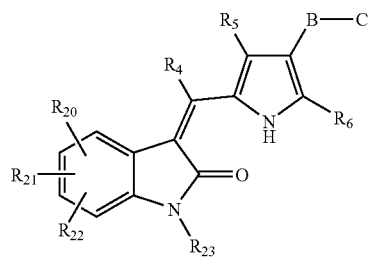
(II)

wherein $R_5$ and $R_6$ are independently selected from hydrogen, $CF_3$, aliphatic or substituted aliphatic; $R_4$, $R_{20}$, $R_{21}$, $R_{22}$, $R_{23}$, G, B and C are as previously defined.

In a third embodiment of the compounds of the present invention are compounds represented by formula (III) as illustrated below, or its geometric isomers, enantiomers, diastereomers, racemates, pharmaceutically acceptable salts, prodrugs and solvates thereof:

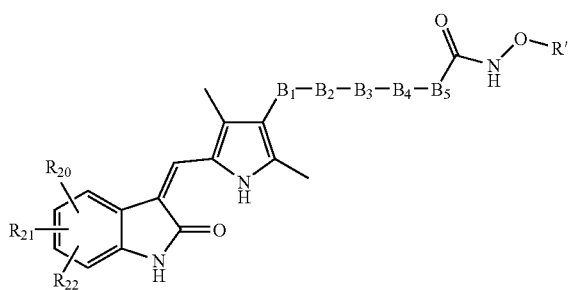

(III)

or its geometric isomers, enantiomers, diastereomers, racemates, pharmaceutically acceptable salts, prodrugs and solvates thereof, Wherein $B_1$ is absent, O, S, SO, $SO_2$, aryl, heteroaryl, heterocyclic, $N(R_8)$, CO; $B_2$ is absent, C1-C6 alkyl, C2-C6 alkenyl, C2-C6 alkynyl, aryl, heteroaryl, heterocyclic, $N(R_8)$, CO, SO, or $SO_2$; $B_3$ is absent, O, $N(R_8)$, CO, $C_1$-$C_6$ alkyl, C2-C6 alkenyl, C2-C6 alkynyl, aryl, heteroaryl, or heterocyclic; $B_4$ is absent, O, S, SO, $SO_2$, $N(R_8)$, CO; $B_5$ is absent, $C_1$-$C_8$ alkyl, $C_2$-$C_8$ alkenyl, $C_2$-$C_8$ alkynyl, heterocyclic, heteroaryl or aryl; and R', $R_{20}$, $R_{21}$, and $R_{22}$ are as previously defined in claim 1.

In a fourth embodiment of the compounds of the present invention are compounds represented by formula (IV) as illustrated below, or its geometric isomers, enantiomers, diastereomers, racemates, pharmaceutically acceptable salts, prodrugs and solvates thereof:

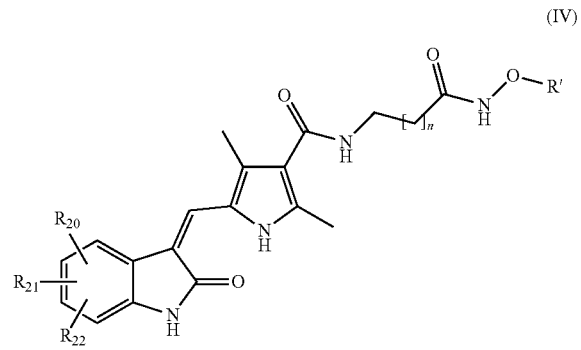

(IV)

wherein n is 1-9; and R', $R_{20}$, $R_{21}$, and $R_{22}$ are as previously defined.

In a fifth embodiment of the compounds of the present invention are compounds represented by formula (V) as illustrated below, or its geometric isomers, enantiomers, diastereomers, racemates, pharmaceutically acceptable salts, prodrugs and solvates thereof:

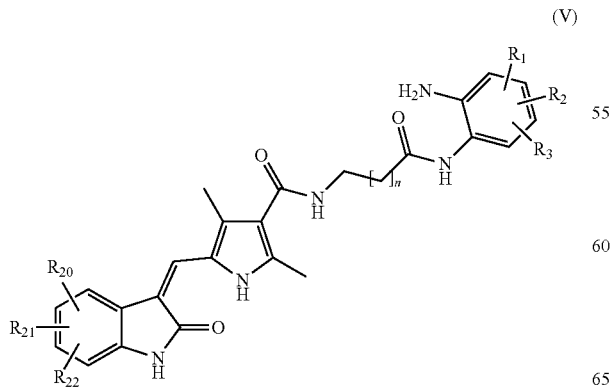

(V)

wherein n is 1-9; $R_1$, $R_2$, $R_3$, $R_{20}$, $R_{21}$, and $R_{22}$ are as previously defined.

In a sixth embodiment of the compounds of the present invention are compounds represented by formula (VI) as illustrated below, or its geometric isomers, enantiomers, diastereomers, racemates, pharmaceutically acceptable salts, prodrugs and solvates thereof:

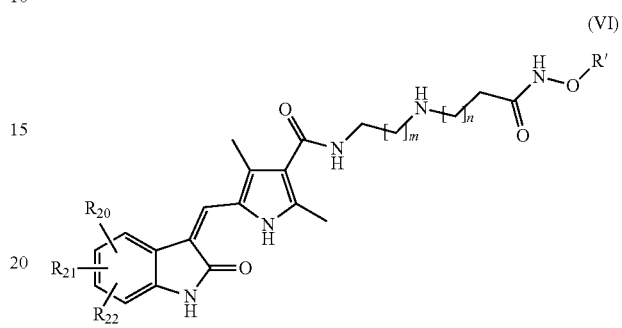

(VI)

wherein n is 1 to 6; m is 1 or 2; R', $R_{20}$, $R_{21}$, and $R_{22}$ are as previously defined.

In a seventh embodiment of the compounds of the present invention are compounds represented by formula (VII) as illustrated below, or its geometric isomers, enantiomers, diastereomers, racemates, pharmaceutically acceptable salts, prodrugs and solvates thereof:

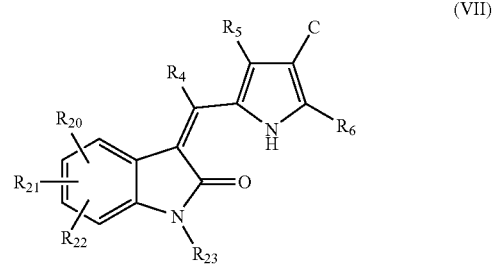

(VII)

wherein C is —C(O)NHOR' or

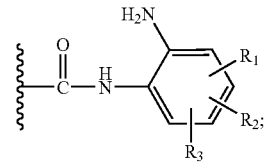

R', $R_4$, $R_5$, $R_6$, $R_{20}$, $R_{21}$, $R_{22}$, and $R_{23}$ are as previously defined.

In an eighth embodiment of the compounds of the present invention are compounds represented by formula (VIII) as illustrated below, or its geometric isomers, enantiomers, diastereomers, racemates, pharmaceutically acceptable salts, prodrugs and solvates thereof:

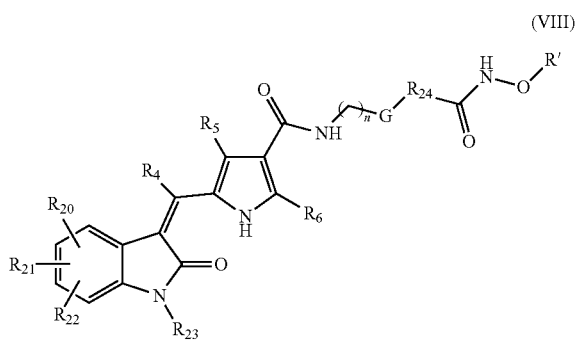

(VIII)

wherein n is 0-7; $R_{24}$ is absent or selected from alkylene, alkenylene, and alkynylene; n is 0-7; G is $Ar_1$, $X_2$—$Ar_1$ or $X_2$-alkyl-$Ar_1$, where $Ar_1$ is independently selected Cy and $X_2$ is O, S or NH; Cy, $R_4$, $R_5$, $R_6$, $R_{20}$, $R_{21}$, $R_{22}$, and $R_{23}$ are as previously defined.

In a ninth embodiment of the compounds of the present invention are compounds represented by formula (IX) as illustrated below, or its geometric isomers, enantiomers, diastereomers, racemates, pharmaceutically acceptable salts, prodrugs and solvates thereof:

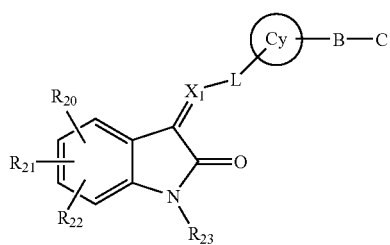

(IX)

or its geometric isomers, enantiomers, diastereomers, racemates, pharmaceutically acceptable salts, prodrugs and solvates thereof, wherein $X_1$ is N, $CR_4$; where $R_4$ is hydrogen or aliphatic;

L is absent or NH;

Cy is an aryl, substituted aryl, heteroaryl, substituted heteroaryl;

B is a direct bond or straight or branched, substituted or unsubstituted alkylene, substituted or unsubstituted alkenylene, substituted or unsubstituted alkynylene, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylheterocyclylalkynyl, alkenylheterocyclylalkyl, alkenylheterocyclylalkenyl, alkenylheterocyclylalkynyl, alkynylheterocyclylalkyl, alkynylheterocyclylalkenyl, or alkynylheterocyclylalkynyl, which one or more methylenes can be interrupted or terminated by O, S, S(O), $SO_2$, $N(R_8)$, C(O), substituted or unsubstituted aryl, substituted or unsubstituted heteroaryl, substituted or unsubstituted heterocyclic; where $R_8$ is hydrogen or aliphatic group;

C is selected from:

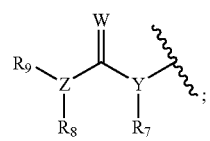

(a)

where W is O or S; Y is absent, N, or CH; Z is N or CH; $R_7$ and $R_9$ are independently hydrogen, hydroxy, aliphatic group, provided that if $R_7$ and $R_9$ are both present, one of $R_7$ or $R_9$ must be hydroxy and if Y is absent, $R_9$ must be hydroxy; and $R_8$ is hydrogen or aliphatic group;

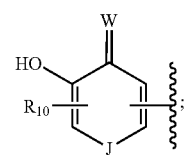

(b)

where W is O or S; J is O, NH or $NCH_3$; and $R_{10}$ is hydrogen or lower alkyl;

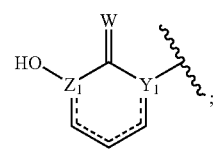

(c)

where W is O or S; $Y_1$ and $Z_1$ are independently N, C or CH; and (d)

where Z, Y, and W are as previously defined; $R_{11}$ and $R_{12}$ are independently selected from hydrogen or aliphatic; $R_1$, $R_2$ and $R_3$ are independently selected from hydrogen, hydroxy, amino, halogen, alkoxy, alkylamino, dialkylamino, $CF_3$, CN, $NO_2$, sulfonyl, acyl, aliphatic, substituted aliphatic, aryl, substituted aryl, heteroaryl, substituted heteroaryl, heterocyclic, and substituted heterocyclic;

$R_{20}$, $R_{21}$, $R_{22}$ are independently selected from hydrogen, hydroxy, $CF_3$, $NO_2$, halogen, lower alkyl, lower alkoxy, lower alkylamino, alkoxyalkoxy (preferably methoxyethoxy), alkylaminoalkoxy (preferably methylaminoethoxy), phenyl, thiophenyl, furanyl, pyrazinyl, substituted pyrazinyl, and morpholino; and $R_{12}$ is selected from hydrogen or lower alkyl; and $R_{23}$ is hydrogen or aliphatic.

In a tenth embodiment of the compounds of the present invention are compounds represented by formula (IX) as illustrated below, or its geometric isomers, enantiomers, diastereomers, racemates, pharmaceutically acceptable salts, prodrugs and solvates thereof:

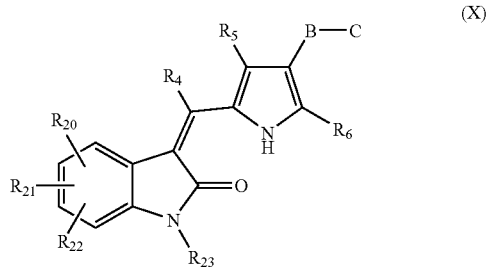

(X)

wherein $R_5$ and $R_6$ are independently selected from hydrogen, $CF_3$, aliphatic or substituted aliphatic; $R_4$, $R_{20}$, $R_{21}$, $R_{22}$, $R_{23}$, G, B and C are as previously defined.

In an eleventh embodiment of the compounds of the present invention are compounds represented by formula (XI) as illustrated below, or its geometric isomers, enantiomers, diastereomers, racemates, pharmaceutically acceptable salts, prodrugs and solvates thereof:

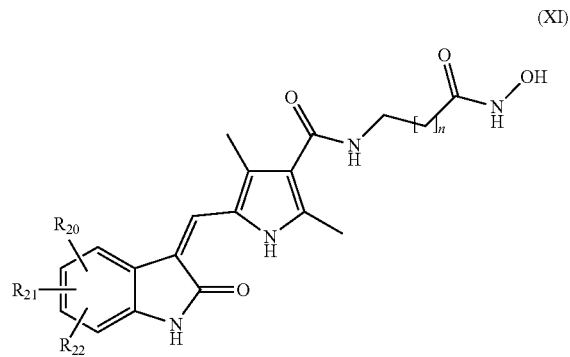

(XI)

wherein n is 1-9; and $R_{20}$, $R_{21}$, and $R_{22}$ are as previously defined.

In a twelfth embodiment of the compounds of the present invention are compounds represented by formula (XII) as illustrated below, or its geometric isomers, enantiomers, diastereomers, racemates, pharmaceutically acceptable salts, prodrugs and solvates thereof:

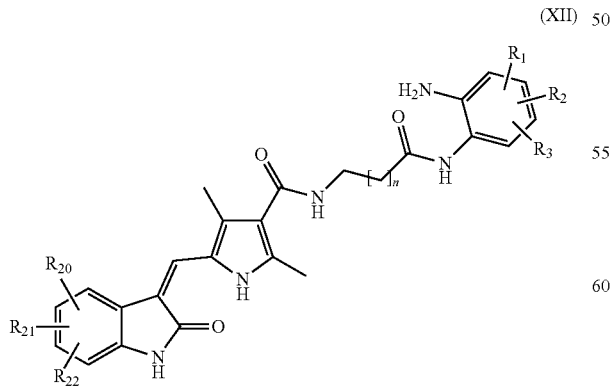

(XII)

wherein n is 1-9; $R_1$, $R_2$, $R_3$, $R_{20}$, $R_{21}$, and $R_{22}$ are as previously defined.

In a thirteenth embodiment of the compounds of the present invention are compounds represented by formula (XIII) as illustrated below, or its geometric isomers, enantiomers, diastereomers, racemates, pharmaceutically acceptable salts, prodrugs and solvates thereof:

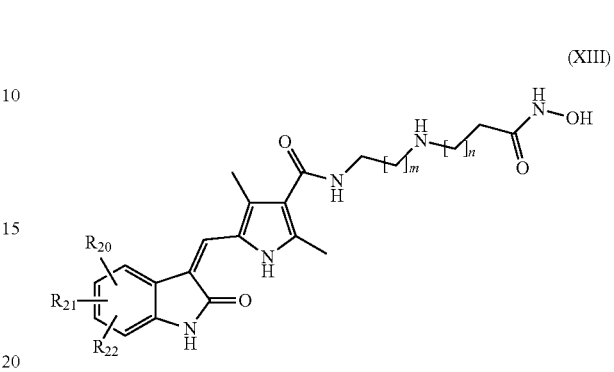

(XIII)

wherein n is 1 to 6; m is 1 or 2; $R_{20}$, $R_{21}$, and $R_{22}$ are as previously defined.

In a fourteenth embodiment of the compounds of the present invention are compounds represented by formula (XIV) as illustrated below, or its geometric isomers, enantiomers, diastereomers, racemates, pharmaceutically acceptable salts, prodrugs and solvates thereof:

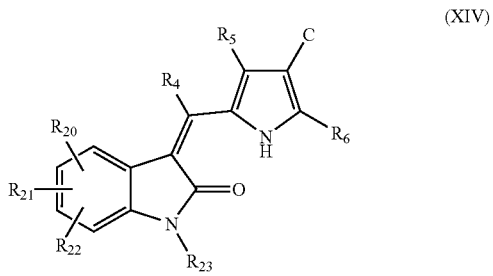

(XIV)

wherein C is —C(O)NHOH or

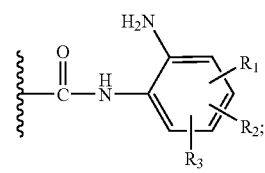

$R_4$, $R_5$, $R_6$, $R_{20}$, $R_{21}$, $R_{22}$, and $R_{23}$ are as previously defined.

In a fifteenth embodiment of the compounds of the present invention are compounds represented by formula (XV) as illustrated below, or its geometric isomers, enantiomers, diastereomers, racemates, pharmaceutically acceptable salts, prodrugs and solvates thereof:

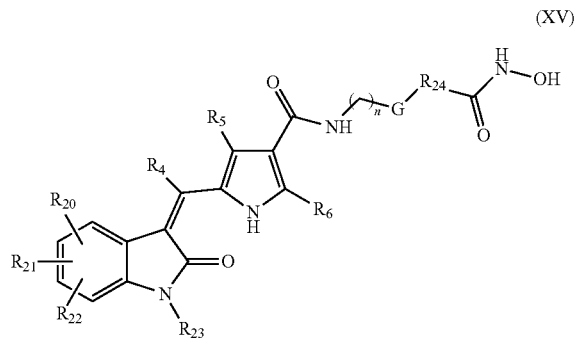

(XV)

wherein n is 0-7; $R_{24}$ is absent or selected from alkylene, alkenylene, and alkynylene; n is 0-7; G is $Ar_1$, $X_2$—$Ar_1$ or $X_2$-alkyl-$Ar_1$, where $Ar_1$ is independently selected Cy and $X_2$ is O, S or NH; Cy, $R_4$, $R_5$, $R_6$, $R_{20}$, $R_{21}$, $R_{22}$, and $R_{23}$ are as previously defined.

Representative compounds according to the invention are those selected from the Table A below or its geometric isomers, enantiomers, diastereomers, racemates, pharmaceutically acceptable salts, prodrugs and solvates thereof:

TABLE A

| Compound No. | Structure |
|---|---|
| 1 | 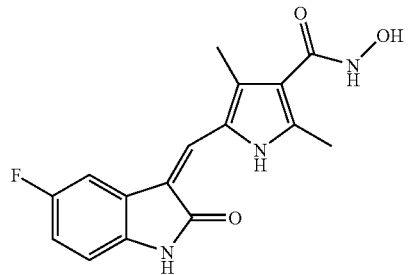 |
| 2 | 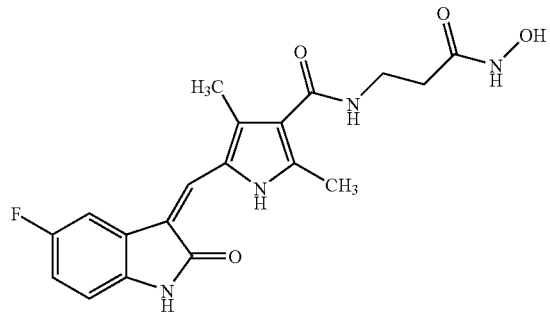 |
| 3 | 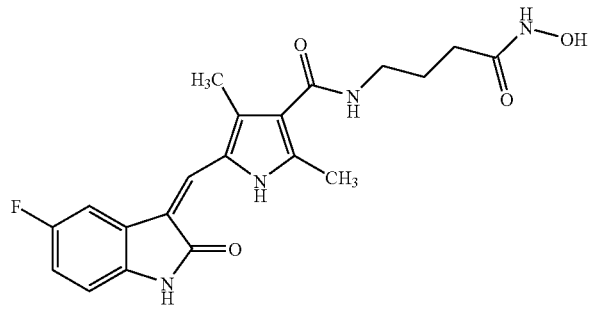 |

TABLE A-continued
| Compound No. | Structure |
|---|---|
| 4 | 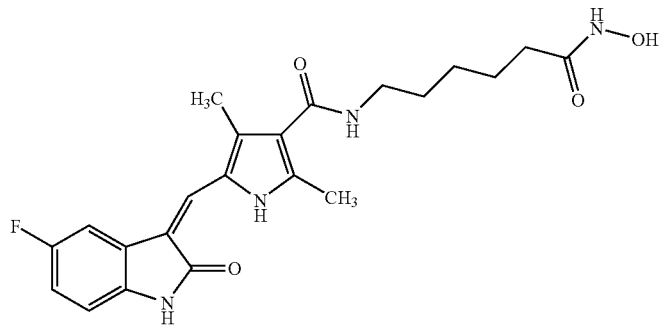 |
| 5 | 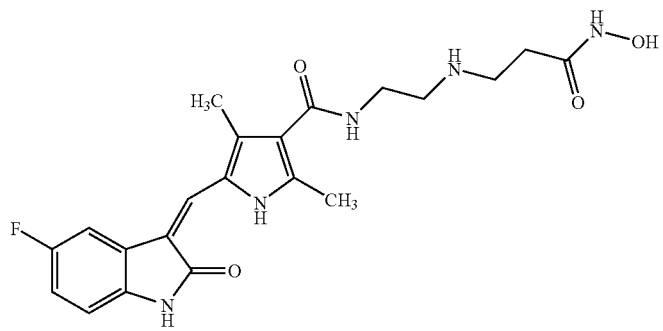 |
| 6 | 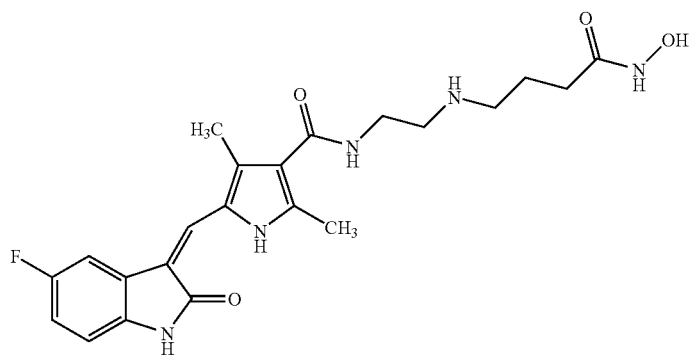 |
| 7 | 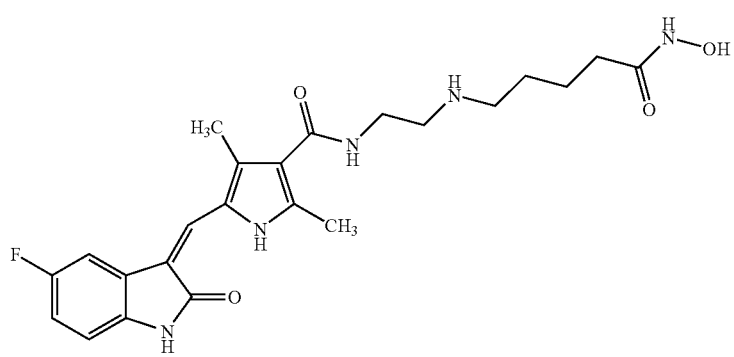 |

TABLE A-continued
| Compound No. | Structure |
|---|---|
| 8 | 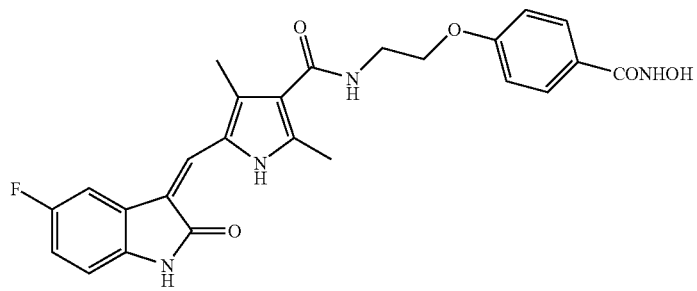 |
| 9 | 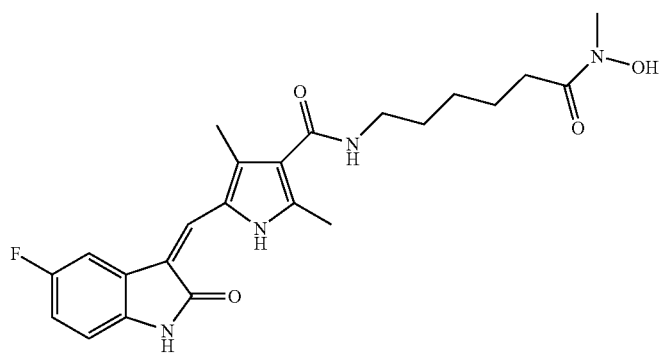 |
| 10 | 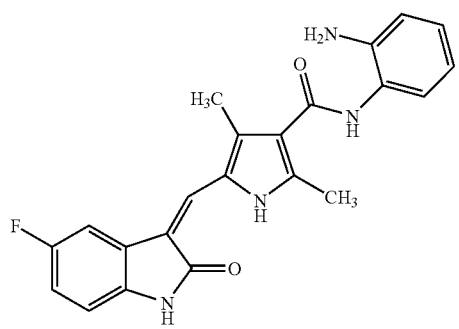 |
| 11 | 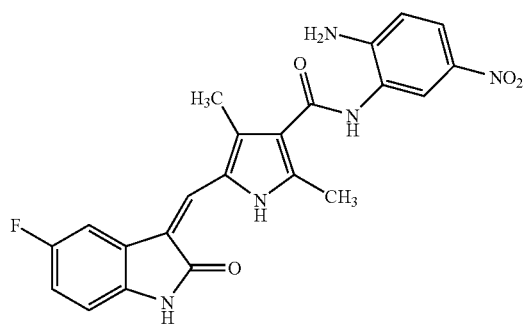 |

TABLE A-continued
| Compound No. | Structure |
|---|---|
| 12 | 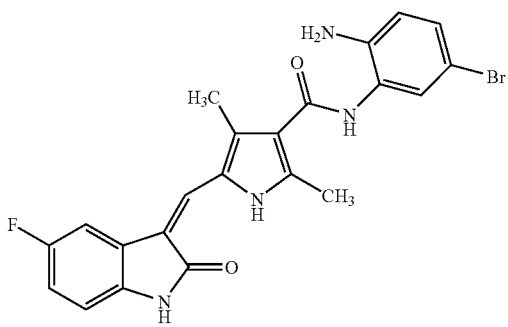 |
| 13 | 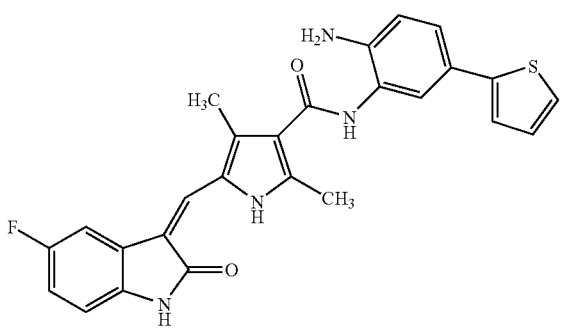 |
| 14 | 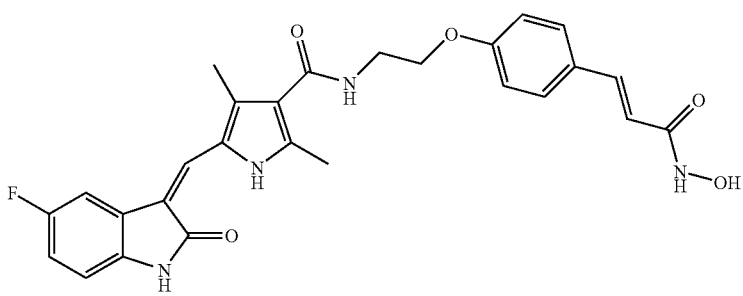 |
| 15 | 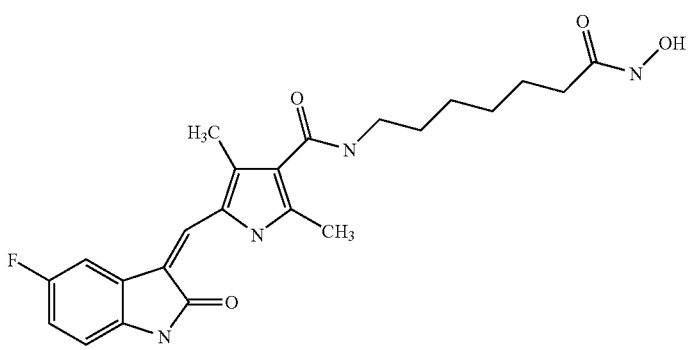 |
| 16 | 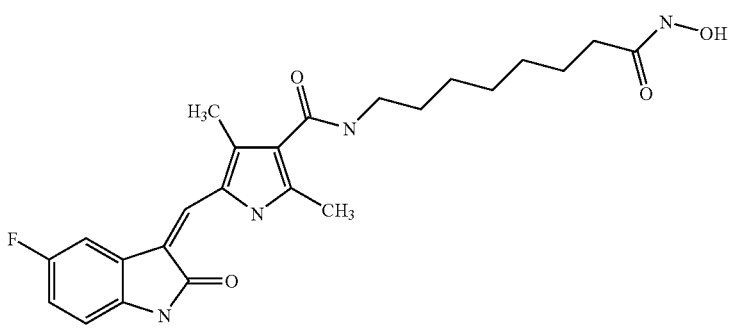 |

TABLE A-continued
| Compound No. | Structure |
|---|---|
| 17 | 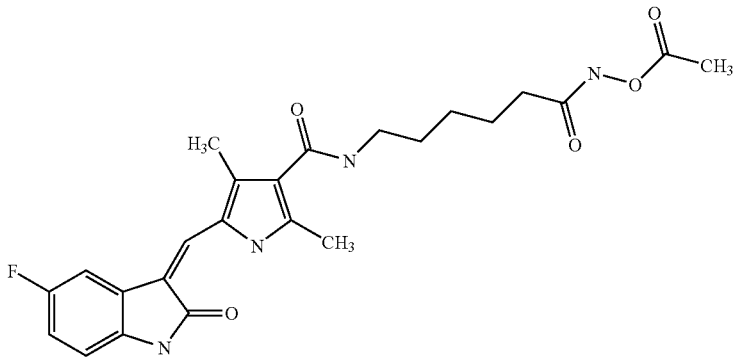 |
| 18 | 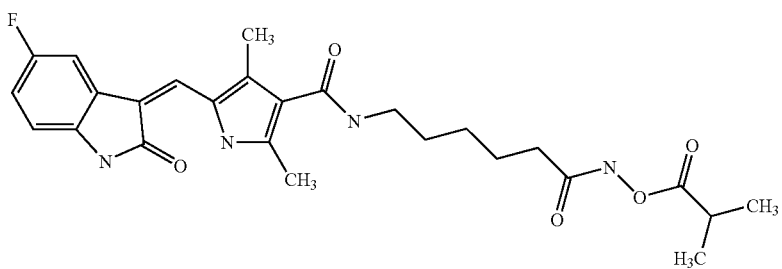 |
| 19 | 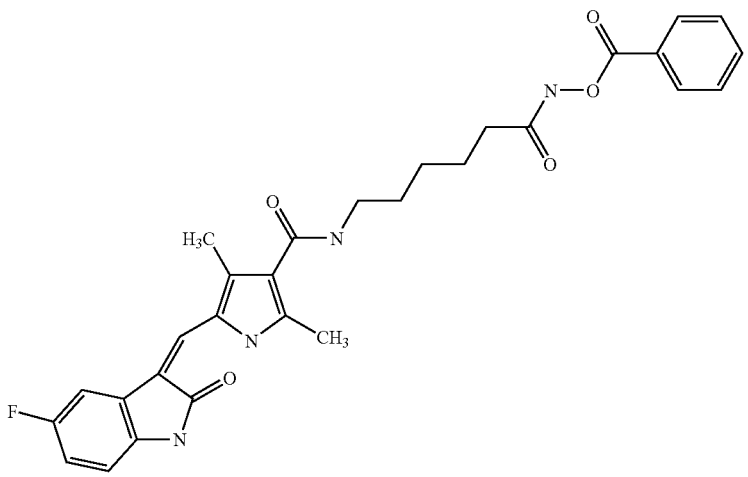 |
| 20 | 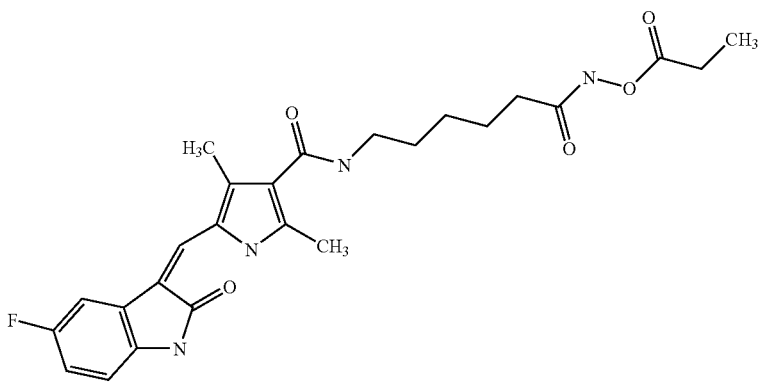 |

TABLE A-continued
| Compound No. | Structure |
|---|---|
| 21 | 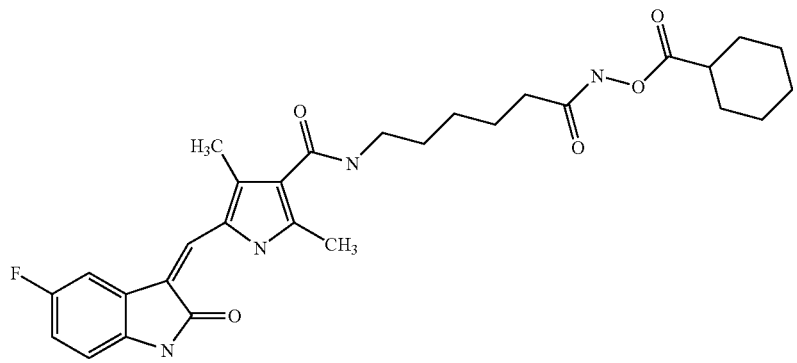 |
| 22 | 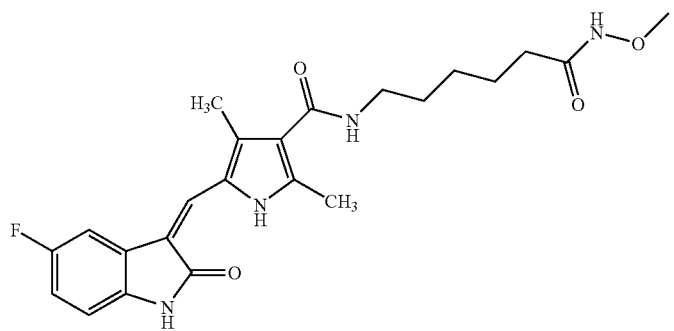 |
| 23 | 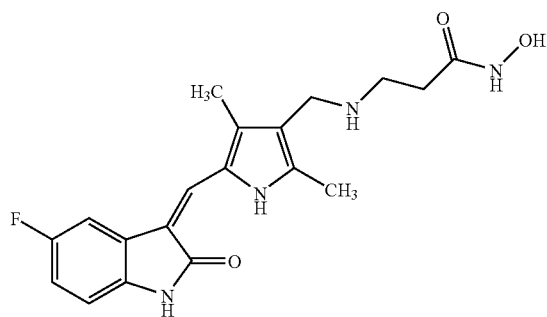 |
| 24 | 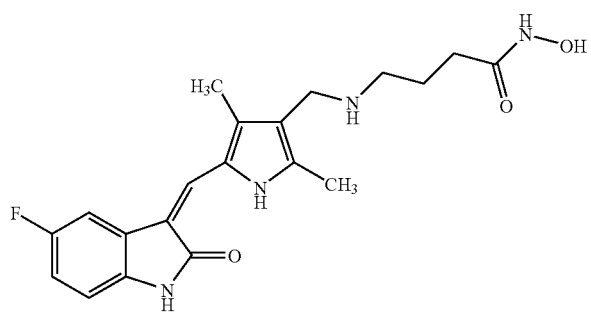 |

TABLE A-continued
| Compound No. | Structure |
|---|---|
| 25 | 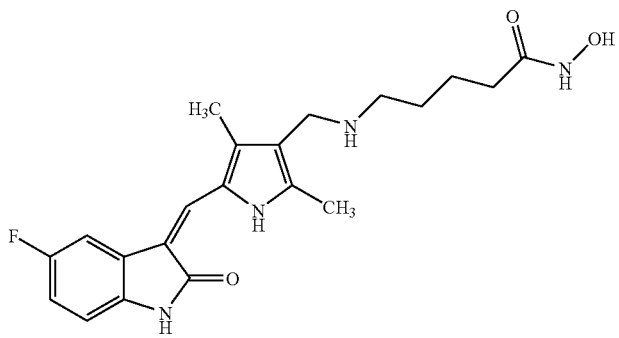 |
| 26 | 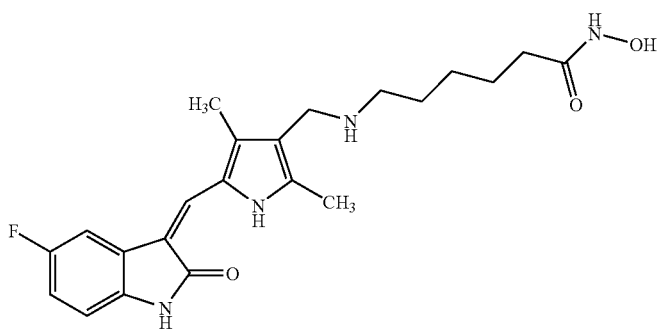 |
| 27 | 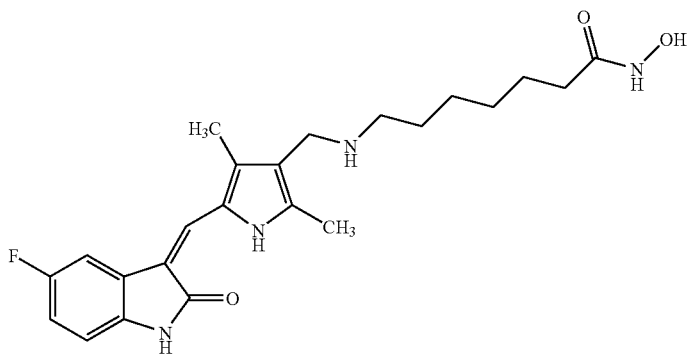 |
| 28 | 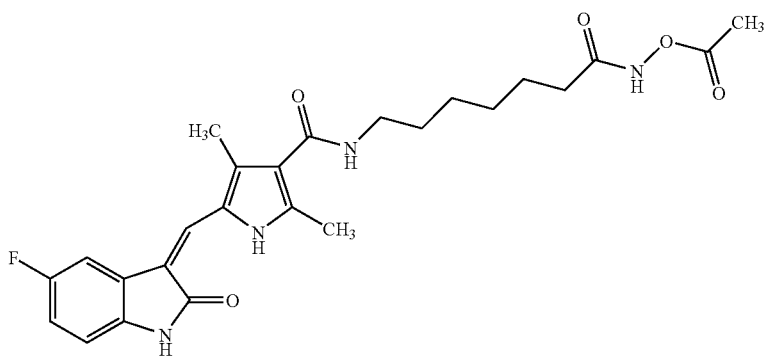 |

TABLE A-continued

Compound No. Structure

29

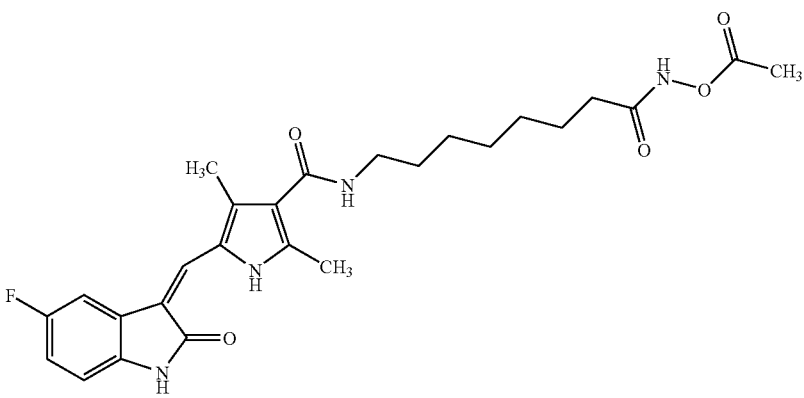

The invention further provides methods for the prevention or treatment of diseases or conditions involving aberrant proliferation, differentiation or survival of cells. In one embodiment, the invention further provides for the use of one or more compounds of the invention in the manufacture of a medicament for halting or decreasing diseases involving aberrant proliferation, differentiation, or survival of cells. In preferred embodiments, the disease is cancer. In one embodiment, the invention relates to a method of treating cancer in a subject in need of treatment comprising administering to said subject a therapeutically effective amount of a compound of the invention.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma, renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the invention, the present invention provides for the use of one or more compounds of the invention in the manufacture of a medicament for the treatment of cancer.

In one embodiment, the present invention includes the use of one or more compounds of the invention in the manufacture of a medicament that prevents further aberrant proliferation, differentiation, or survival of cells. For example, compounds of the invention may be useful in preventing tumors from increasing in size or from reaching a metastatic state. The subject compounds may be administered to halt the progression or advancement of cancer or to induce tumor apoptosis or to inhibit tumor angiogenesis. In addition, the instant invention includes use of the subject compounds to prevent a recurrence of cancer.

This invention further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intra-epithelial tissue.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In one aspect of the invention, the subject compounds may be administered in combination with one or more separate agents that modulate protein kinases involved in various disease states. Examples of such kinases may include, but are not limited to: serine/threonine specific kinases, receptor tyrosine specific kinases and non-receptor tyrosine specific kinases. Serine/threonine kinases include mitogen activated protein kinases (MAPK), meiosis specific kinase (MEK), RAF and aurora kinase. Examples of receptor kinase families include epidermal growth factor receptor (EGFR) (e.g. HER2/neu, HER3, HER4, ErbB, ErbB2, ErbB3, ErbB4, Xmrk, DER, Let23); fibroblast growth factor (FGF) receptor (e.g. FGF-R1, GFF-R2/BEK/CEK3, FGF-R3/CEK2, FGF-R4/TKF, KGF-R); hepatocyte growth/scatter factor receptor (HGFR) (e.g, MET, RON, SEA, SEX); insulin receptor (e.g. IGFI-R); Eph (e.g. CEK5, CEK8, EBK, ECK, EEK, EHK-1, EHK-2, ELK, EPH, ERK, HEK, MDK2, MDK5, SEK); Axl (e.g. Mer/Nyk, Rse); RET; and platelet-derived growth factor receptor (PDGFR) (e.g. PDGFα-R, PDGFβ-R, CSF1-R/FMS, SCF-R/C-KIT, VEGF-R/FLT, NEK/FLK1, FLT3/FLK2/STK-1). Non-receptor tyrosine kinase families include, but are not limited to, BCR-ABL (e.g. p43abl, ARG); BTK (e.g. ITK/EMT, TEC); CSK, FAK, FPS, JAK, SRC, BMX, FER, CDK and SYK.

In another aspect of the invention, the subject compounds may be administered in combination with one or more separate agents that modulate non-kinase biological targets or processes. Such targets include histone deacetylases (HDAC), DNA methyltransferase (DNMT), heat shock proteins (e.g. HSP90), and proteosomes.

In a preferred embodiment, subject compounds may be combined with antineoplastic agents (e.g. small molecules, monoclonal antibodies, antisense RNA, and fusion proteins) that inhibit one or more biological targets such as Zolinza, Tarceva, Iressa, Tykerb, Gleevec, Sutent, Sprycel, Nexavar, Sorafinib, CNF2024, RG108, BMS387032, Affinitak, Avastin, Herceptin, Erbitux, AG24322, PD325901, ZD6474, PD184322, Obatodax, ABT737 and AEE788. Such combinations may enhance therapeutic efficacy over efficacy achieved by any of the agents alone and may prevent or delay the appearance of resistant mutational variants.

In certain preferred embodiments, the compounds of the invention are administered in combination with a chemotherapeutic agent. Chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cylophosphamide, chlorambucil, melphalan, ifosfamide), ethylenimines (thiotepa, hexamethylmelanine), Alkylsulfonates (Busulfan), Hydrazines and Triazines (Altretamine, Procarbazine, Dacarbazine and Temozolomide), Nitrosoureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine, Vindesine and Vinorelbine), and Camptothecan analogs (Irinotecan and Topotecan); anti-tumor antibiotics such as Chromomycins (Dactinomycin and Plicamycin), Anthracyclines (Doxorubicin, Daunorubicin, Epirubicin, Mitoxantrone, Valrubicin and Idarubicin), and miscellaneous antibiotics such as Mitomycin, Actinomycin and Bleomycin; anti-metabolites such as folic acid antagonists (Methotrexate, Pemetrexed, Raltitrexed, Aminopterin), pyrimidine antagonists (5-Fluorouracil, Floxuridine, Cytarabine, Capecitabine, and Gemcitabine), purine antagonists (6-Mercaptopurine and 6-Thioguanine) and adenosine deaminase inhibitors (Cladribine, Fludarabine, Mercaptopurine, Clofarabine, Thioguanine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan, Cetuximab, Panitumumab, Tositumomab, Bevacizumab); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA)).

In certain preferred embodiments, the compounds of the invention are administered in combination with a chemoprotective agent. Chemoprotective agents act to protect the body or minimize the side effects of chemotherapy. Examples of such agents include, but are not limited to, amfostine, mesna, and dexrazoxane.

In one aspect of the invention, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

It will be appreciated that compounds of the invention can be used in combination with an immunotherapeutic agent. One form of immunotherapy is the generation of an active systemic tumor-specific immune response of host origin by administering a vaccine composition at a site distant from the tumor. Various types of vaccines have been proposed, including isolated tumor-antigen vaccines and anti-idiotype vaccines. Another approach is to use tumor cells from the subject to be treated, or a derivative of such cells (reviewed by Schirrmacher et al. (1995) J. Cancer Res. Clin. Oncol. 121:487). In U.S. Pat. No. 5,484,596, Hanna Jr. et al. claim a method for treating a respectable carcinoma to prevent recurrence or metastases, comprising surgically removing the tumor, dispersing the cells with collagenase, irradiating the cells, and vaccinating the patient with at least three consecutive doses of about 107 cells.

It will be appreciated that the compounds of the invention may advantageously be used in conjunction with one or more adjunctive therapeutic agents. Examples of suitable agents for adjunctive therapy include a 5HT1 agonist, such as a triptan (e.g. sumatriptan or naratriptan); an adenosine A1 agonist; an EP ligand; an NMDA modulator, such as a glycine antagonist; a sodium channel blocker (e.g. lamotrigine); a substance P antagonist (e.g. an NK1 antagonist); a cannabinoid; acetaminophen or phenacetin; a 5-lipoxygenase inhibitor; a leukotriene receptor antagonist; a DMARD (e.g. methotrexate); gabapentin and related compounds; a tricyclic antidepressant (e.g. amitryptilline); a neurone stabilising antiepileptic drug; a mono-aminergic uptake inhibitor (e.g. venlafaxine); a matrix metalloproteinase inhibitor; a nitric oxide synthase (NOS) inhibitor, such as an iNOS or an nNOS inhibitor; an inhibitor of the release, or action, of tumour necrosis factor .alpha.; an antibody therapy, such as a monoclonal antibody therapy; an antiviral agent, such as a nucleoside inhibitor (e.g. lamivudine) or an immune system modulator (e.g. interferon); an opioid analgesic; a local anaesthetic; a stimulant, including caffeine; an H2-antagonist (e.g. ranitidine); a proton pump inhibitor (e.g. omeprazole); an antacid (e.g. aluminium or magnesium hydroxide); an antiflatulent (e.g. simethicone); a decongestant (e.g. phenylephrine, phenylpropanolamine, pseudoephedrine, oxymetazoline, epinephrine, naphazoline, xylometazoline, propylhexedrine, or levo-desoxyephedrine); an antitussive (e.g. codeine, hydrocodone, carmiphen, carbetapentane, or dextramethorphan); a diuretic; or a sedating or non-sedating antihistamine.

Matrix metalloproteinases (MMPs) are a family of zinc-dependent neutral endopeptidases collectively capable of degrading essentially all matrix components. Over 20 MMP modulating agents are in pharmaceutical develop, almost half of which are indicated for cancer. The University of Toronto researchers have reported that HDACs regulate MMP expression and activity in 3T3 cells. In particular, inhibition of HDAC by trichostatin A (TSA), which has been shown to prevent tumorigenesis and metastasis, decreases mRNA as well as zymographic activity of gelatinase A (MMP2; Type IV collagenase), a matrix metalloproteinase, which is itself, implicated in tumorigenesis and metastasis (Ailenberg M., Silverman M., Biochem Biophys Res Commun. 2002, 298: 110-115). Another recent article that discusses the relationship of HDAC and MMPs can be found in Young D. A., et al., Arthritis Research & Therapy, 2005, 7: 503. Furthermore, the commonality between HDAC and MMPs inhibitors is their zinc-binding functionality. Therefore, in one aspect of the invention, compounds of the invention can be used as MMP inhibitors and may be of use in the treatment of disorders relating to or associated with dysregulation of MMP. The overexpression and activation of MMPs are known to induce tissue destruction and are also associated with a number of specific diseases including rheumatoid arthritis, periodontal disease, cancer and atherosclerosis.

The compounds may also be used in the treatment of a disorder involving, relating to or, associated with dysregulation of histone deacetylase (HDAC). There are a number of disorders that have been implicated by or known to be mediated at least in part by HDAC activity, where HDAC activity is known to play a role in triggering disease onset, or whose symptoms are known or have been shown to be alleviated by HDAC inhibitors. Disorders of this type that would be expected to be amenable to treatment with the compounds of the invention include the following but not limited to: Antiproliferative disorders (e.g. cancers); Neurodegenerative diseases including Huntington's Disease, Polyglutamine disease, Parkinson's Disease, Alzheimer's Disease, Seizures, Striatonigral degeneration, Progressive supranuclear palsy, Torsion dystonia, Spasmodic torticollis and dyskinesis, Familial tremor, Gilles de la Tourette syndrome, Diffuse Lewy body disease, Progressive supranuclear palsy, Pick's disease, intracerebral hemorrhage, Primary lateral sclerosis, Spinal muscular atrophy, Amyotrophic lateral sclerosis, Hypertrophic interstitial polyneuropathy, Retinitis pigmentosa, Hereditary optic atrophy, Hereditary spastic paraplegia, Progressive ataxia and Shy-Drager syndrome; Metabolic diseases including Type 2 diabetes; Degenerative Diseases of the Eye including Glaucoma, Age-related macular degeneration, Rubeotic glaucoma; Inflammatory diseases and/or Immune system disorders including Rheumatoid Arthritis (RA), Osteoarthritis, Juvenile chronic arthritis, Graft versus Host disease, Psoriasis, Asthma, Spondyloarthropathy, Crohn's Disease, inflammatory bowel disease Colitis Ulcerosa, Alcoholic hepatitis, Diabetes, Sjoegrens's syndrome, Multiple Sclerosis, Ankylosing spondylitis, Membranous glomerulopathy, Discogenic pain, Systemic Lupus Erythematosus; Disease involving angiogenesis including cancer, psoriasis, rheumatoid arthritis; Psychological disorders including bipolar disease, schizophrenia, mania, depression and dementia; Cardiovascular Diseases including heart failure, restenosis and arteriosclerosis; Fibrotic diseases including liver fibrosis, cystic fibrosis and angiofibroma; Infectious diseases including Fungal infections, such as *Candida Albicans*, Bacterial infections, Viral infections, such as Herpes Simplex, Protozoal infections, such as Malaria, *Leishmania infection, Trypanosoma brucei* infection, Toxoplasmosis and coccidlosis and Haematopoietic disorders including thalassemia, anemia and sickle cell anemia.

In one embodiment, compounds of the invention can be used to induce or inhibit apoptosis, a physiological cell death process critical for normal development and homeostasis. Alterations of apoptotic pathways contribute to the pathogenesis of a variety of human diseases. Compounds of the invention, as modulators of apoptosis, will be useful in the treatment of a variety of human diseases with abberations in apoptosis including cancer (particularly, but not limited to, follicular lymphomas, carcinomas with p53 mutations, hormone dependent tumors of the breast, prostate and ovary, and precancerous lesions such as familial adenomatous polyposis), viral infections (including, but not limited to, herpesvirus, poxvirus, Epstein-Barr virus, Sindbis virus and adenovirus), autoimmune diseases (including, but not limited to, systemic lupus, erythematosus, immune mediated glomerulonephritis, rheumatoid arthritis, psoriasis, inflammatory bowel diseases, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including, but not limited to, chronic anemia and aplastic anemia), degenerative diseases of the musculoskeletal system (including, but not limited to, osteoporosis and arthritis), aspirin-sensitive rhinosinusitis, cystic fibrosis, multiple sclerosis, kidney diseases, and cancer pain.

In one aspect, the invention provides the use of compounds of the invention for the treatment and/or prevention of immune response or immune-mediated responses and diseases, such as the prevention or treatment of rejection following transplantation of synthetic or organic grafting materials, cells, organs or tissue to replace all or part of the function of tissues, such as heart, kidney, liver, bone marrow, skin, cornea, vessels, lung, pancreas, intestine, limb, muscle, nerve tissue, duodenum, small-bowel, pancreatic-islet-cell, including xeno-transplants, etc.; to treat or prevent graft-versus-host disease, autoimmune diseases, such as rheumatoid arthritis, systemic lupus erythematosus, thyroiditis, Hashimoto's thyroiditis, multiple sclerosis, myasthenia gravis, type I diabetes uveitis, juvenile-onset or recent-onset diabetes mellitus, uveitis, Graves disease, psoriasis, atopic dermatitis, Crohn's disease, ulcerative colitis, vasculitis, auto-antibody mediated diseases, aplastic anemia, Evan's syndrome, autoimmune hemolytic anemia, and the like; and further to treat infectious diseases causing aberrant immune response and/or activation, such as traumatic or pathogen induced immune disregulation, including for example, that which are caused by hepatitis B and C infections, HIV, *staphylococcus aureus* infection, viral encephalitis, sepsis, parasitic diseases wherein damage is induced by an inflammatory response (e.g., leprosy); and to prevent or treat circulatory diseases, such as arteriosclerosis, atherosclerosis, vasculitis, polyarteritis nodosa and myocarditis. In addition, the present invention may be used to prevent/suppress an immune response associated with a gene therapy treatment, such as the introduction of foreign genes into autologous cells and expression of the encoded product. Thus in one embodiment, the invention relates to a method of treating an immune response disease or disorder or an immune-mediated response or disorder in a subject in need of treatment comprising administering to said subject a therapeutically effective amount of a compound of the invention.

In one aspect, the invention provides the use of compounds of the invention in the treatment of a variety of neurodegenerative diseases, a non-exhaustive list of which includes: I. Disorders characterized by progressive dementia in the absence of other prominent neurologic signs, such as Alzheimer's disease; Senile dementia of the Alzheimer type; and Pick's disease (lobar atrophy); II. Syndromes combining progressive dementia with other prominent neurologic abnormalities such as A) syndromes appearing mainly in adults (e.g., Huntington's disease, Multiple system atrophy combining dementia with ataxia and/or manifestations of Parkinson's disease, Progressive supranuclear palsy (Steel-Richardson-Olszewski), diffuse Lewy body disease, and corticodentatonigral degeneration); and B) syndromes appearing mainly in children or young adults (e.g., Hallervorden-Spatz disease and progressive familial myoclonic epilepsy); III. Syndromes of gradually developing abnormalities of posture and movement such as paralysis agitans (Parkinson's disease), striatonigral degeneration, progressive supranuclear palsy, torsion dystonia (torsion spasm; dystonia musculorum deformans), spasmodic torticollis and other dyskinesis, familial tremor, and Gilles de la Tourette syndrome; IV. Syndromes of progressive ataxia such as cerebellar degenerations (e.g., cerebellar cortical degeneration and olivopontocerebellar atrophy (OPCA)); and spinocerebellar degeneration (Friedreich's atazia and related disorders); V. Syndrome of central autonomic nervous system failure (Shy-Drager syndrome); VI. Syndromes of muscular weakness and wasting without sensory changes (motorneuron disease such as amyotrophic lateral sclerosis, spinal muscular atrophy (e.g., infantile spinal muscular atrophy (Werdnig-Hoffman), juvenile spinal muscular atrophy (Wohlfart-Kugelberg-Welander) and other forms of familial spinal muscular atrophy), primary lateral sclerosis, and hereditary spastic paraplegia; VII. Syndromes combining muscular weakness and wasting with sensory changes (progressive neural muscular atrophy; chronic familial polyneuropathies) such as peroneal muscular atrophy (Charcot-Marie-Tooth), hypertrophic interstitial polyneuropathy (Dejerine-Sottas), and miscellaneous forms of chronic progressive neuropathy; VIII Syndromes of progressive visual loss such as pigmentary degeneration of the retina (retinitis pigmentosa), and hereditary optic atrophy (Leber's disease). Furthermore, compounds of the invention can be implicated in chromatin remodeling.

The invention encompasses pharmaceutical compositions comprising pharmaceutically acceptable salts of the compounds of the invention as described above. The invention also encompasses pharmaceutical compositions comprising hydrates of the compounds of the invention. The term "hydrate" includes but is not limited to hemihydrate, monohydrate, dihydrate, trihydrate and the like. The invention further encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

The compounds of the invention, and derivatives, fragments, analogs, homologs, pharmaceutically acceptable salts or hydrate thereof can be incorporated into pharmaceutical compositions suitable for administration, together with a pharmaceutically acceptable carrier or excipient. Such compositions typically comprise a therapeutically effective amount of any of the compounds above, and a pharmaceutically acceptable carrier. Preferably, the effective amount when treating cancer is an amount effective to selectively induce terminal differentiation of suitable neoplastic cells and less than an amount which causes toxicity in a patient.

Compounds of the invention may be administered by any suitable means, including, without limitation, parenteral, intravenous, intramuscular, subcutaneous, implantation, oral, sublingual, buccal, nasal, pulmonary, transdermal, topical, vaginal, rectal, and transmucosal administrations or the like. Topical administration can also involve the use of transdermal administration such as transdermal patches or iontophoresis devices. Pharmaceutical preparations include a solid, semi-solid or liquid preparation (tablet, pellet, troche, capsule, suppository, cream, ointment, aerosol, powder, liquid, emulsion, suspension, syrup, injection etc.) containing a compound of the invention as an active ingredient, which is suitable for selected mode of administration. In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, sachets and effervescent, powders, and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the active compound and the inert carrier or diluent, a hard gelatin capsule.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and may additionally comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Daily administration may be repeated continuously for a period of several days to several years. Oral treatment may continue for between one week and the life of the patient. Preferably the administration may take place for five consecutive days after which time the patient can be evaluated to determine if further administration is required. The administration can be continuous or intermittent, i.e., treatment for a number of consecutive days followed by a rest period. The compounds of the present invention may be administered intravenously on the first day of treatment, with oral administration on the second day and all consecutive days thereafter.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In one embodiment, the concentration of the compound in the patient's plasma is maintained at about 25 nM. In one embodiment, the concentration of the compound in the patient's plasma is maintained at about 50 nM. In one embodiment, the concentration of the compound in the patient's plasma is maintained at about 100 nM. In one embodiment, the concentration of the compound in the patient's plasma is maintained at about 500 nM. In one embodiment, the concentration of the compound in the patient's plasma is maintained at about 1000 nM. In one embodiment, the concentration of the compound in the patient's plasma is maintained at about 2500 nM. In one embodiment, the concentration of the compound in the patient's plasma is maintained at about 5000 nM. The optimal amount of the compound that should be administered to the patient in the practice of the present invention will depend on the particular compound used and the type of cancer being treated.

DEFINITIONS

Listed below are definitions of various terms used to describe this invention. These definitions apply to the terms as they are used throughout this specification and claims, unless otherwise limited in specific instances, either individually or as part of a larger group.

An "aliphatic group" or "aliphatic" is non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. An aliphatic group preferably contains between about 1 and about 24 atoms, more preferably between about 4 to about 24 atoms, more preferably between about 4-12 atoms, more typically between about 4 and about 8 atoms.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as ($C_1$-$C_6$)alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about eight carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about ten carbon atoms and more preferably about two to about eight carbon atoms. Examples of alkenyl radicals include ethenyl, allyl, propenyl, butenyl and 4-methylbutenyl. The terms "alkenyl", and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about ten carbon atoms and more preferably about two to eight carbon atoms. Examples of alkynyl radicals include propargyl, 1-propynyl, 2-propynyl, 1-butyne, 2-butynyl and 1-pentynyl.

The term "cycloalkyl" embraces saturated carbocyclic radicals having three to about twelve carbon atoms. The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl.

The term "cycloalkenyl" embraces partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The terms "alkoxy" embrace linear or branched oxy-containing radicals each having alkyl portions of one to about twenty carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" embraces alkyl radicals having one or more alkoxy radicals attached to the alkyl radical, that is, to form monoalkoxyalkyl and dialkoxyalkyl radicals.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The term "carbonyl", whether used alone or with other terms, such as "alkoxycarbonyl", denotes (C=O).

The term "carbanoyl", whether used alone or with other terms, such as "arylcarbanoylyalkyl", denotes C(O)NH.

The terms "heterocyclyl", "heterocycle" "heterocyclic" or "heterocyclo" embrace saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" embraces heterocyclo-substituted alkyl radicals. More preferred heterocycloalkyl radicals are "lower heterocycloalkyl" radicals having one to six carbon atoms within heterocyclo radicals.

The term "alkylthio" embraces radicals containing a linear or branched alkyl radical, of one to about ten carbon atoms attached to a divalent sulfur atom. Preferred alkylthio radicals have alkyl radicals of one to about twenty carbon atoms or, preferably, one to about twelve carbon atoms. More preferred alkylthio radicals have alkyl radicals are "lower alkylthio" radicals having one to about ten carbon atoms. Most preferred are alkylthio radicals having lower alkyl radicals of one to about eight carbon atoms. Examples of such lower alkylthio radicals are methylthio, ethylthio, propylthio, butylthio and hexylthio.

The terms "aralkyl" or "arylalkyl" embrace aryl-substituted alkyl radicals such as benzyl, diphenylmethyl, triphenylmethyl, phenylethyl, and diphenylethyl.

The term "aryloxy" embraces aryl radicals attached through an oxygen atom to other radicals.

The terms "aralkoxy" or "arylalkoxy" embrace aralkyl radicals attached through an oxygen atom to other radicals.

The term "aminoalkyl" embraces alkyl radicals substituted with amino radicals. Preferred aminoalkyl radicals have alkyl radicals having about one to about twenty carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N,N-alkylamino, such as N-methylamino, N-ethylamino, N,N-dimethylamino, N,N-diethylamino or the like.

The term "linker" means an organic moiety that connects two parts of a compound. Linkers typically comprise a direct bond or an atom such as oxygen or sulfur, a unit such as $NR_8$, $C(O)$, $C(O)NH$, $SO$, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylheterocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylherероaryl, which one or more methylenes can be interrupted or terminated by O, S, S(O), $SO_2$, $N(R_8)$, $C(O)$, substituted or unsubstituted aryl, substituted or unsubstituted heteroaryl, substituted or unsubstituted heterocyclic; where $R_8$ is hydrogen, acyl, aliphatic or substituted aliphatic. In one embodiment, the linker B is between 1-24 atoms, preferably 4-24 atoms, preferably 4-18 atoms, more preferably 4-12 atoms, and most preferably about 4-10 atoms.

The term "substituted" refers to the replacement of one or more hydrogen radicals in a given structure with the radical of a specified substituent including, but not limited to, halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is further understood that each of the substituent listed above can be further substituted.

For simplicity, chemical moieties are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

As used herein, the term "aberrant proliferation" refers to abnormal cell growth.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The term "angiogenesis," as used herein, refers to the formation of blood vessels. Specifically, angiogenesis is a multi-step process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., Adv. Cancer Res., Vol. 43, pp. 175-203 (1985)). Anti-angiogenic agents interfere with this process. Examples of agents that interfere with several of these steps include thrombospondin-1, angiostatin, endostatin, interferon alpha and compounds such as matrix metalloproteinase (MMP) inhibitors that block the actions of enzymes that clear and create paths for newly forming blood vessels to follow; compounds, such as .alpha.v.beta.3 inhibitors, that interfere with molecules that blood vessel cells use to bridge between a parent blood vessel and a tumor; agents, such as specific COX-2 inhibitors, that prevent the growth of cells that form new blood vessels; and protein-based compounds that simultaneously interfere with several of these targets.

The term "apoptosis" as used herein refers to programmed cell death as signaled by the nuclei in normally functioning human and animal cells when age or state of cell health and condition dictates. An "apoptosis inducing agent" triggers the process of programmed cell death.

The term "cancer" as used herein denotes a class of diseases or disorders characterized by uncontrolled division of cells and the ability of these cells to invade other tissues, either by direct growth into adjacent tissue through invasion or by implantation into distant sites by metastasis.

The term "compound" is defined herein to include pharmaceutically acceptable salts, solvates, hydrates, polymorphs, enantiomers, diastereoisomers, racemates and the like of the compounds having a formula as set forth herein.

The term "devices" refers to any appliance, usually mechanical or electrical, designed to perform a particular function.

As used herein, the term "dysplasia" refers to abnormal cell growth.

As used herein, the term "effective amount of the subject compounds," with respect to the subject method of treatment, refers to an amount of the subject compound which, when delivered as part of desired dose regimen, brings about, e.g. a change in the rate of cell proliferation and/or state of differentiation and/or rate of survival of a cell to clinically acceptable standards. This amount may further relieve to some extent one or more of the symptoms of a neoplasia disorder, including, but is not limited to: 1) reduction in the number of cancer cells; 2) reduction in tumor size; 3) inhibition (i.e., slowing to some extent, preferably stopping) of cancer cell infiltration into peripheral organs; 3) inhibition (i.e., slowing to some extent, preferably stopping) of tumor metastasis; 4) inhibition, to some extent, of tumor growth; 5) relieving or reducing to some extent one or more of the symptoms associated with the disorder; and/or 6) relieving or reducing the side effects associated with the administration of anticancer agents.

The term "hyperplasia," as used herein, refers to excessive cell division or growth.

The phrase an "immunotherapeutic agent" refers to agents used to transfer the immunity of an immune donor, e.g., another person or an animal, to a host by inoculation. The term embraces the use of serum or gamma globulin containing performed antibodies produced by another individual or an animal; nonspecific systemic stimulation; adjuvants; active specific immunotherapy; and adoptive immunotherapy. Adoptive immunotherapy refers to the treatment of a disease by therapy or agents that include host inoculation of sensitized lymphocytes, transfer factor, immune RNA, or antibodies in serum or gamma globulin.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention.

The term "metastasis," as used herein, refers to the migration of cancer cells from the original tumor site through the blood and lymph vessels to produce cancers in other tissues. Metastasis also is the term used for a secondary cancer growing at a distant site.

The term "neoplasm," as used herein, refers to an abnormal mass of tissue that results from excessive cell division. Neoplasms may be benign (not cancerous), or malignant (cancerous) and may also be called a tumor. The term "neoplasia" is the pathological process that results in tumor formation.

As used herein, the term "pre-cancerous" refers to a condition that is not malignant, but is likely to become malignant if left untreated.

The term "proliferation" refers to cells undergoing mitosis.

The phrase "PTK related disease or disorder" refers to a disease or disorder characterized by inappropriate PTK activity or over-activity of the PTK. Inappropriate activity refers to either; (i) PTK expression in cells which normally do not express PTKs; (ii) increased PTK expression leading to unwanted cell proliferation, differentiation and/or growth; or, (iii) decreased PTK expression leading to unwanted reductions in cell proliferation, differentiation and/or growth. Over-activity of PTKs refers to either amplification of the gene encoding a particular PTK or production of a level of PTK activity which can correlate with a cell proliferation, differentiation and/or growth disorder (that is, as the level of the PTK increases, the severity of one or more of the symptoms of the cellular disorder increases). Over activity can also be the result of ligand independent or constitutive activation as a result of mutations such as deletions of a fragment of PTK responsible for ligand binding.

The phrase a "radiotherapeutic agent" refers to the use of electromagnetic or particulate radiation in the treatment of neoplasia.

The term "recurrence" as used herein refers to the return of cancer after a period of remission. This may be due to incomplete removal of cells from the initial cancer and may occur locally (the same site of initial cancer), regionally (in vicinity of initial cancer, possibly in the lymph nodes or tissue), and/or distally as a result of metastasis.

The term "treatment" refers to any process, action, application, therapy, or the like, wherein a mammal, including a human being, is subject to medical aid with the object of improving the mammal's condition, directly or indirectly.

The term "vaccine" includes agents that induce the patient's immune system to mount an immune response against the tumor by attacking cells that express tumor associated antigens (TAAs).

As used herein, the term "effective amount of the subject compounds," with respect to the subject method of treatment, refers to an amount of the subject compound which, when delivered as part of desired dose regimen, brings about, e.g. a change in the rate of cell proliferation and/or state of differentiation and/or rate of survival of a cell to clinically acceptable standards. This amount may further relieve to some extent one or more of the symptoms of a neoplasia disorder, including, but is not limited to: 1) reduction in the number of cancer cells; 2) reduction in tumor size; 3) inhibition (i.e., slowing to some extent, preferably stopping) of cancer cell infiltration into peripheral organs; 3) inhibition (i.e., slowing to some extent, preferably stopping) of tumor metastasis; 4) inhibition, to some extent, of tumor growth; 5) relieving or reducing to some extent one or more of the symptoms associated with the disorder; and/or 6) relieving or reducing the side effects associated with the administration of anticancer agents.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "pre-cancerous" refers to a condition that is not malignant, but is likely to become malignant if left untreated.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers and/or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha- ($\alpha$), beta-(B) and gamma-($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al, and WO 98/43,650 by Montgomery, all of which are incorporated herein by reference). A discussion of pulmonary delivery of antibiotics is also found in U.S. Pat. No. 6,014,969, incorporated herein by reference.

By a "therapeutically effective amount" of a compound of the invention is meant an amount of the compound which confers a therapeutic effect on the treated subject, at a reasonable benefit/risk ratio applicable to any medical treatment.

The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Synthetic Methods

The compounds of the invention may be prepared by any process known to be applicable to the preparation of chemically-related compounds. Suitable processes for making certain intermediates include, for example, those illustrated in references such as, *J. Med Chem.* 2003, 46, 1116-1119 and *J. Med Chem.* 2003, 68, 6447-6450. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of a chemist.

The compounds and processes of the present invention will be better understood in connection with the following representative synthetic scheme that illustrate the methods by which the compounds of the invention may be prepared, which are intended as an illustration only and not limiting of the scope of the invention.

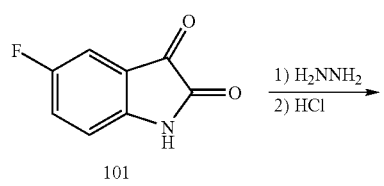

Scheme 1

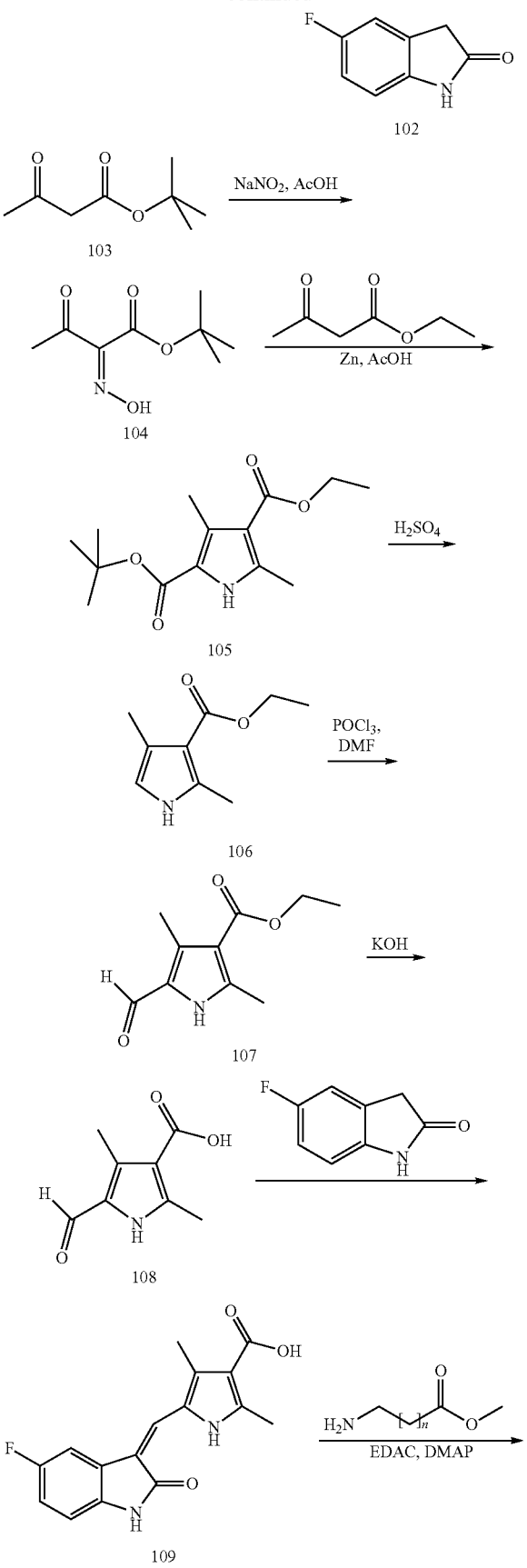

51
-continued
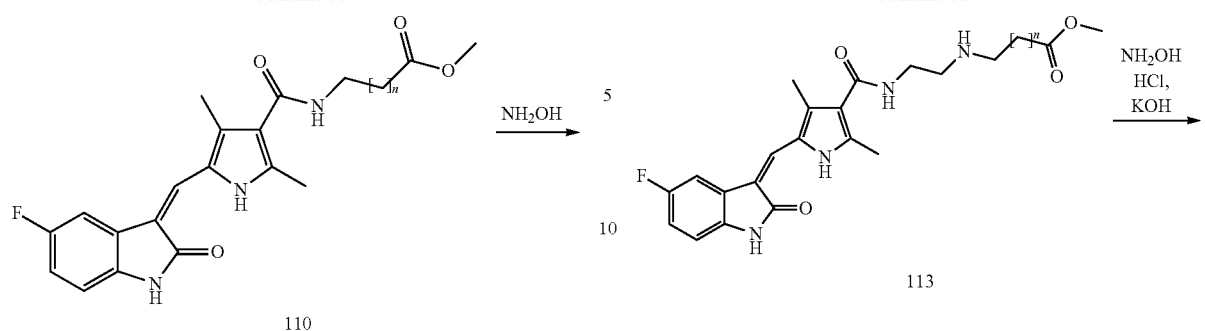
110
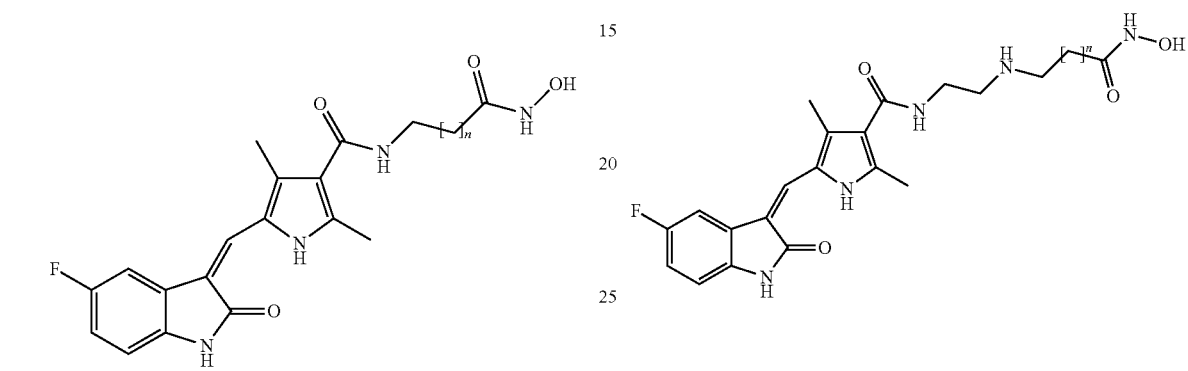
109
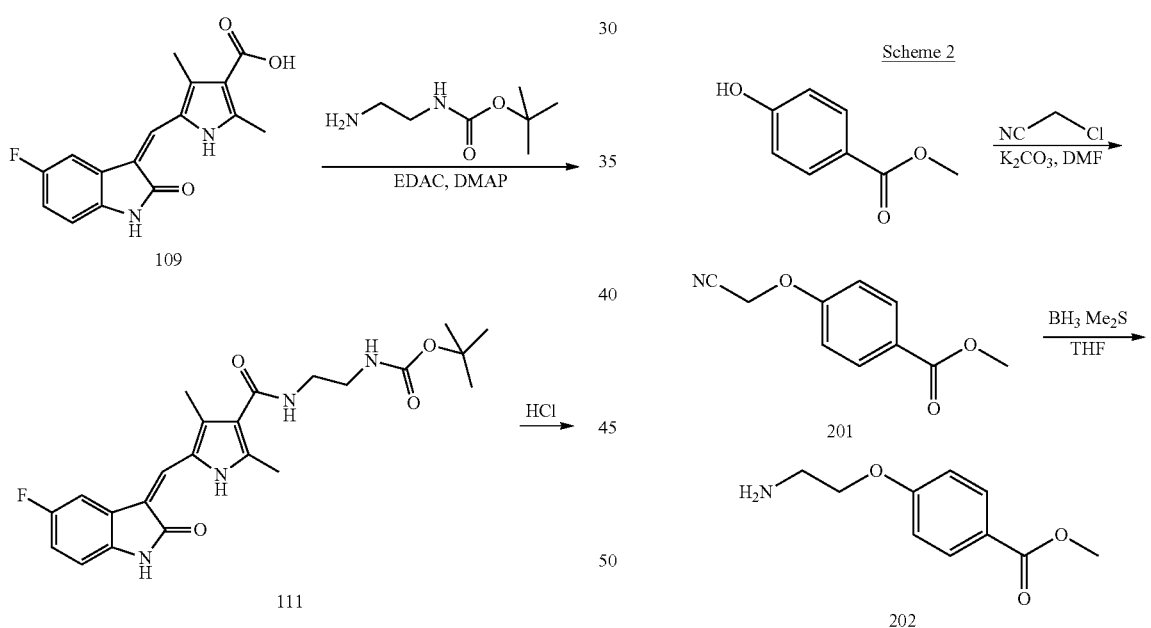
111
112
52
-continued
113
Scheme 2
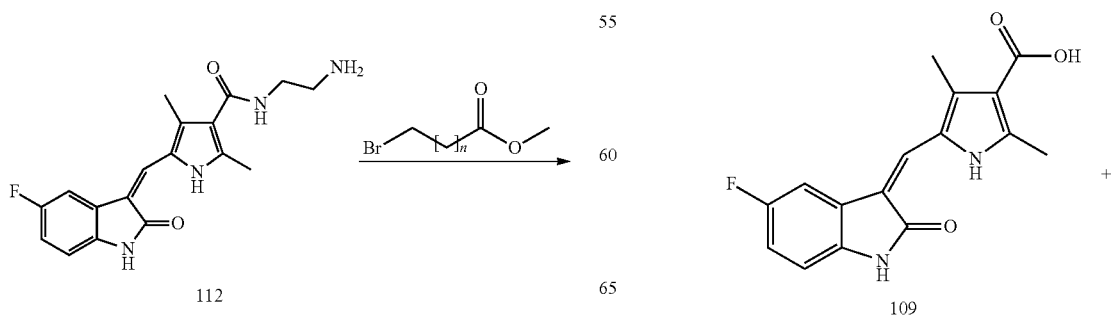
201
202
109

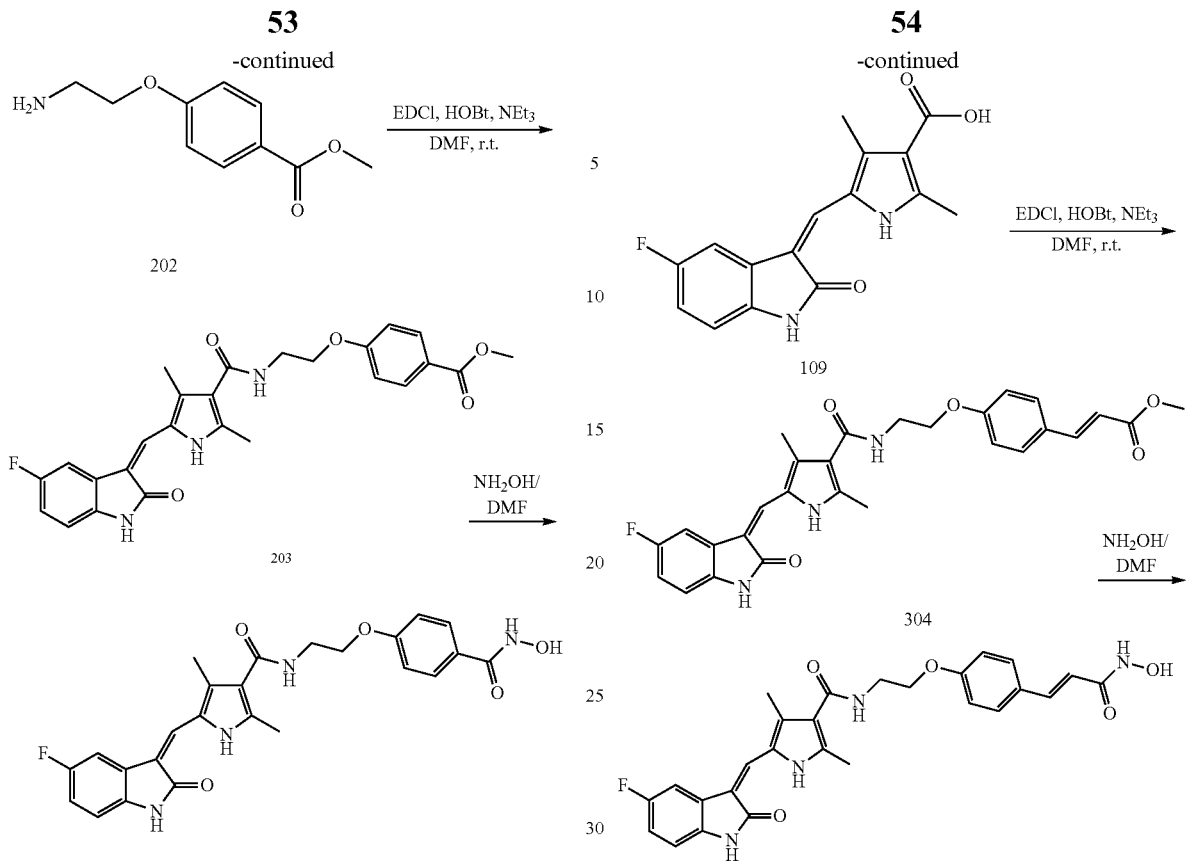

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Preparation of 5-((Z)-(5-fluoro-2-oxoindolin-3-ylidene)methyl)-N-hydroxy-2,4-dimethyl-1H-pyrrole-3-carboxamide (compound 1)

Step 1a. 5-fluoroindolin-2-one (compound 102)

KOH (4.07 g, 73 mmol) was added into a mixture of compound 101 (6.0 g, 36 mmol), ethyleneglycol (95 mL) and hydrazine hydrate (2.6 g, 52 mmol). The reaction mixture was stirred at 80° C. for 3 h, and then was cooled to room temperature and was poured to ice cold water. The pH of the above mixture was adjusted to pH 1-2 with 12 N hydrochloric acid and the mixture was stirred at room temperature for 12 h. The mixture was then extracted with EtOAc. The organic phase was collected, evaporated to give yellow solid product 102 (4.5 g. 81.9%). LCMS: m/z 152(M+1), $^1$HNMR (DMSO-$d_6$) δ3.46 (s, 2H), 6.95 (m, 3H), 10.35 (s, 1H).

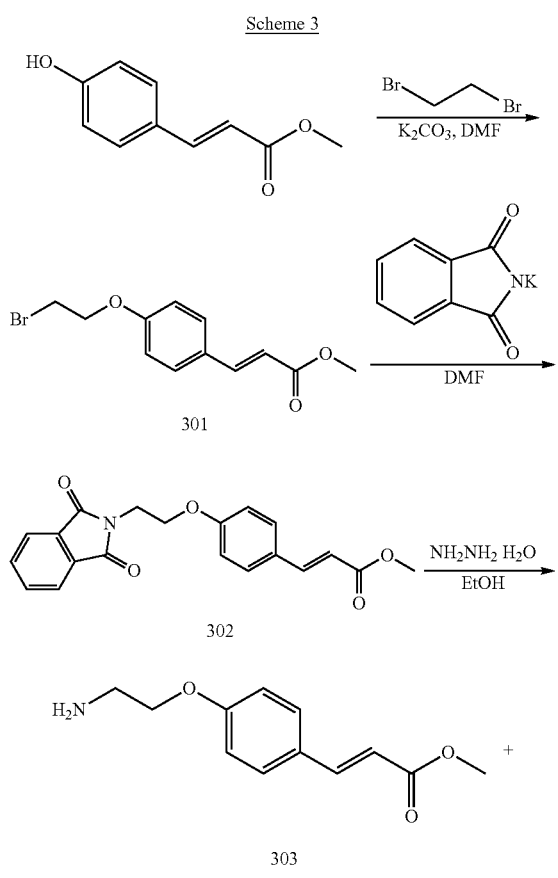

Scheme 3

Step 1b. tert-Butyl 2-(hydroxyimino)-3-oxobutanoate (compound 104)

To a solution of compound 103 (69.52 g, 44 mol) in glacial acetic acid (500 mL) cooled to 5° C. was added dropwise a cold solution of sodium nitrite (32.5 g, 0.446 mol) in water (50 mL). The mixture was stirred for 1 h and allowed to stand for 4 h, during which time it warmed to room temperature. The mixture was used in the next step without further purification. LCMS: m/z 188(M+1).

Step 1c. 2-tert-Butyl 4-ethyl 3,5-dimethyl-1H-pyrrole-2,4-dicarboxylate (Compound 105)

The above mixture (104) was stirred and portions of zinc powder (84 g, 1.29 mol) were added at such a rate that the mixture temperature was blow 80° C. After the addition was completed, the mixture was heated to 60° C. for 1 h. Ethyl acetylacetate (60 g, 0.46 mol) was added into above mixture and the mixture was refluxed at 85° C. for 4 h. The mixture was filtered to remove the zinc powder when it was hot, the filtrate was poured into 1 L of ice and stand overnight. The precipitate was filtered to obtain product 105 (29 g, 24.7%), the solid was used in next step without further purification. LCMS: m/z 268(M+1).

Step 1d. Ethyl 2,4-dimethyl-1H-pyrrole-3-carboxylate (Compound 106)

A solution of 105 (12 g, 45 mmol) in ethanol (325 mL) was treated with 1 M $H_2SO_4$ (240 mL). The solution was stirred at 65° C. for 4 h, and then cooled to room temperature and evaporated most of ethanol, extracted with dichloromethane. The organic layer was combined and dried with $MgSO_4$. After removal of the solvent, the crude product 506 (3 g, 40%) was obtained. The crude product was purified by column chromatography (silica gel, elution 10/1 petroleum/ethyl acetate) to obtain brown solid product 106 (1.5 g, 20%). LCMS: m/z 168(M+1), $^1$H NMR (DMSO-$d_6$) δ2.10(s, 3H), 2.35 (s, 3H), 4.13 (q, 2H), 6.37 (s, 1H), 10.85 (s, 1H).

Step 1e. Ethyl 5-formyl-2,4-dimethyl-1H-pyrrole-3-carboxylate (Compound 107)

To a solution of DMF (2 g, 27 mmol) at 10° C. was added $POCl_3$ (2.6 mL) in 10 mL of dichloromethane through the dropping funnel over a period of 30 min. After addition, the mixture was stirred for 20 min at room temperature. Dichloromethane (10 mL) was added into the mixture. When the internal temperature lowed to 5° C., a solution of compound 506 in dichloromethane (10 mL) was added through a dropping funnel to the stirred, cooled mixture over a period of 1 h, then the mixture was stirred at the reflux temperature for 30 min, the mixture was then cooled to 30° C., a solution of sodium acetate (17 g, 125 mmol) in water (100 ml) was added. The reaction mixture was again refluxed for 30 min. then cooled to room temperature, the aqueous layer was extracted with dichloromethane (4×100 mL). The combined organic layer were washed with brine, dried and evaporated to give gray solid product 107 (4.42 g, 90%). LCMS: m/z 196 (M+1), $^1$HNMR (DMSO-$d_6$) δ1.35 (t, J3H), 2.23 (s, 3H), 2.48 (s, 3H), 4.12 (q, 2H), 9.60 (s, 1H), 10.58 (s, 1H).

Step 1f. 5-Formyl-2,4-dimethyl-1H-pyrrole-3-carboxylic Acid (compound 108)

A solution of KOH (6.2 g, 111 mmol) in water (400 mL) was added to a solution of compound 507 (7.2 g, 37 mmol) in ethanol (60 mL). The mixture was refluxed until the reaction was completed. The mixture was cooled to room temperature and the aqueous layer was extracted with dichloromethane. The aqueous layer was acidified to pH=2 with 1N HCl. The precipitate was collected by filtration, washed with water and dried to give yellow solid product 108 (5.5 g, 89%). LCMS: m/z 168(M+1), $^1$H NMR (DMSO-$d_6$) δ2.40 (s, 3H), 2.43 (s, 3H), 9.24 (s, 1H), 12.14 (bs, 2H).

Step 1g. 5-((Z)-(5-fluoro-2-oxoindolin-3-ylidene) methyl)-N-hydroxy-2,4-dimethyl-1H-pyrrole-3-carboxamide (compound 1)

A mixture of compound 108 (4.0 g. 24 mmol), 102 (3.6 g 24 mmol) and pyrrolidine (2 mL) in ethanol (200 mL) was stirred and heated at 78° C. for 6 h. The mixture was filtered to give yellow solid, dried to yield product 1 (5.5 g, 77%). LCMS: m/z 301(M+1), $^1$H NMR (DMSO-$d_6$) δ2.39 (s, 3H), 2.42 (s, 3H), 6.82 (m, 2H), 7.77 (s, 1H), 7.80 (m, 1H), 10.93 (s, 1H), 12.23 (s, 1H), 13.86 (s, 1H).

Example 2

Preparation of N-(2-(hydroxycarbamoyl)ethyl)-5-((Z)-(5-fluoro-2-oxoindolin-3-ylidene)methyl)-2,4-dimethyl-1H-pyrrole-3-carboxamide (compound 2)

Step 2a. Methyl 3-(5-((Z)-(5-fluoro-2-oxoindolin-3-ylidene)methyl)-2,4-dimethyl-1H-pyrrole-3-carboxamido)propanoate (compound 110-2)

To a stirred solution of 1 (0.5 g, 1.67 mmol) in DMF (35 mL) at room temperature was added HOBt (1.02 g, 7.52 mmol), triethylamine (2.12 mL, 15.03 mmol), ECDI.HCl (1.44 g, 1.52 mmol) and methyl 3-aminopropanate hydrochloride (0.7 g, 5.0 mmol) successively. The mixture was stirred for 24 h at room temperature and then was diluted with water (20 mL), brine (20 mL) and saturated bicarbonate solution (20 mL) and the pH of solution was adjusted to 11~12 with 10 mol/L NaOH. The mixture was filtrated and the solid was collected washed with water, dried to obtain crude yellow solid product 110-2 (0.44 g, 68.3%). LCMS: m/z 386(M+1), $^1$H NMR (DMSO-$d_6$) δ2.38 (s, 3H), 2.41 (s, 3H), 2.50 (t, 2H), 3.44 (t, 2H), 3.62 (s, 3H), 6.85 (m, 2H), 7.71 (m, 3H), 10.86 (s, 1H), 13.69 (s, 1H).

Step 2b. N-(2-(Hydroxycarbamoyl)ethyl)-5-((Z)-(5-fluoro-2-oxoindolin-3-ylidene)methyl)-2,4-dimethyl-1H-pyrrole-3-carboxamide (compound 2)

NaH (60%, 936 mg, 23.4 mmol g) was added to the solution of hydroxy-ammonium chloride (1.08 g, 15.6 mmol) in DMF (25 mL) drop portion at ice bath. After 0.5 h, the solution of 110-2 (0.2 g, 0.52 mmol) in DMSO (3 mL) was added to the above mixture. The mixture was stirred for 2 h at 0° C., filtration, the residue was washed with DMF, and the DMF was removed under reduce pressure, purified to obtain yellow solid 2 (25 mg, 12.5%). LCMS: m/z 387(M+1), $^1$H NMR (DMSO-$d_6$) δ2.25(t, 2H) 2.41 (s, 3H), 2.43 (s, 3H), 6.85 (m, 2H), 7.64 (t, 1H), 7.71 (s, 1H), 7.727 (m, 1H), 8.75 (s, 1H), 10.47 (s, 1H), 10.89 (s, 1H), 13.68 (s, 1H).

Example 3

Preparation of N-(3-(hydroxycarbamoyl)propyl)-5-((Z)-(5-fluoro-2-oxoindolin-3-ylidene)methyl)-2,4-dimethyl-1H-pyrrole-3-carboxamide (compound 3)

Step 3a. Methyl 4-(5-((Z)-(5-fluoro-2-oxoindolin-3-ylidene)methyl)-2,4-dimethyl-1H-pyrrole-3-carboxamido)butanoate (Compound 110-3)

To a stirred solution of compound 1 (0.5 g, 1.67 mmol) in DMF (35 mL) at room temperature was added HOBt (1.02 g, 7.52 mmol), triethylamine (2.12 mL, 15.03 mmol), ECDI·HCl (1.44 g, 1.52 mmol) and methyl 4-aminobutanate hydrochloride (0.77 g, 5.0 mmol) successively. The mixture was stirred for 24 h at room temperature and then was diluted with water (20 mL), brine (20 mL) and saturated bicarbonate solution (20 mL) and the pH of solution was adjusted to 11~12 with 10 mol/L NaOH. The mixture was filtrated, the solid was collected, washed with water and dried to obtain crude yellow solid product 110-3 (0.32 g, 48.3%). LCMS: m/z 400(M+1), $^1$H NMR (DMSO-$d_6$) δ1.77 (m, 2H), 2.39 (m, 4H), 2.42 (s, 3H), 2.49 (s, 3H), 3.23 (t, 2H), 6.85 (m, 2H), 7.60 (t, 1H), 7.67 (s, 1H), 7.71 (m, 1H), 10.89 (s, 1H), 13.68 (s, 1H).

Step 3b. N-(3-(Hydroxycarbamoyl)propyl)-5-((Z)-(5-fluoro-2-oxoindolin-3-ylidene)methyl)-2,4-dimethyl-1H-pyrrole-3-carboxamide (compound 3)

NaH (60%, 900 mg, 22.5 mmol g) was added to a solution of hydroxyamine hydrochloride (1.04 g, 15 mmol) in DMF (25 mL) portionwise at ice bath. After 0.5 h, the solution of compound 110-3 (0.2 g, 0.5 mmol) in DMSO (3 mL) was added to the above mixture. The mixture was stirred for 2 h at 0° C. The reaction was filtered and the residue was washed with DMF, dried to remove remaining DMF to yield yellow solid product 3 (21.0 mg, 10.5%). LCMS: m/z 401(M+1), $^1$HNMR (DMSO-$d_6$) δ1.73 (t, 2H), 2.02 (t, 2H), 2.38 (s, 3H), 2.41 (s, 3H), 2.43 (t, 2H), 6.85 (m, 2H), 7.66 (t, 1H), 7.72 (s, 1H), 7.76 (m, 1H), 8.70 (s, 1H), 10.40 (s, 1H), 10.88 (s, 1H), 13.68 (s, 1H).

Example 4

Preparation of N-(5-(hydroxycarbamoyl)pentyl)-5-((Z)-(5-fluoro-2-oxoindolin-3-ylidene)methyl)-2,4-dimethyl-1H-pyrrole-3-carboxamide (compound 4)

Step 4a. Methyl 6-(5-((Z)-(5-fluoro-2-oxoindolin-3-ylidene)methyl)-2,4-dimethyl-1H-pyrrole-3-carboxamido)hexanoate (compound 110-4)

To a stirred solution of compound 1 (0.5 g, 1.67 mmol) in DMF (35 mL) at room temperature was added HOBt (1.02 g, 7.52 mmol), triethylamine (2.12 mL, 15.03 mmol), ECDI·HCl (1.44 g, 1.52 mmol) and methyl 6-aminohexanate hydrochloride (0.91 g, 5.0 mmol) successively. The mixture was stirred for 24 h at room temperature and then was diluted with water (20 mL), brine (20 mL) and saturated bicarbonate solution (20 mL) and the pH of solution was adjusted to 11~12 with 10 M NaOH. The mixture was filtrated and the resulting solid was washed with water and dried to obtain crude yellow solid product 110-4 (0.47 g, 65.8%). LCMS: m/z 428(M+1), $^1$H NMR (DMSO-$d_6$) δ1.33 (m, 2H), 1.54 (m, 4H), 2.32 (t, 2H), 2.42 (s, 3H), 2.50 (s, 3H), 3.20 (t, 2H), 3.59 (s, 3H), 6.85 (m, 2H), 7.60 (t, 1H), 7.69 (s, 1H), 7.71 (m, 1H), 10.88 (s, 1H), 13.67 (s, 1H).

Step 4b. N-(5-(Hydroxycarbamoyl)pentyl)-5-((Z)-(5-fluoro-2-oxoindolin-3-ylidene)methyl)-2,4-dimethyl-1H-pyrrole-3-carboxamide (compound 4)

NaH (60%, 846 mg, 21.3 mmol g) was added to the solution of hydroxyamine hydrochloride (0.93 g, 14.0 mmol) in DMF (25 mL) portionwise at 0° C. After 0.5 h, the solution of 110-4 (0.2 g, 0.47 mmol) in DMSO (3 mL) was added to the above mixture. The mixture was stirred for 2 h at 0° C. and filtered. The collected solid was washed with DMF, and the remaining DMF was removed under reduce pressure to obtain yellow solid product 4 (22.6 mg, 11.2%). m.p. 209.7° C. (decompose), LCMS: m/z 429(M+1), $^1$H NMR (DMSO-$d_6$) δ1.27 (m, 2H), 1.48 (m, 4H), 1.94 (t, 2H), 2.38 (s, 3H), 2.40 (s, 3H), 3.12 (t, 2H), 6.87 (m, 2H), 7.60 (t, 1H), 7.69 (s, 1H), 7.72 (m, 1H), 8.63 (s, 1H), 10.32 (s, 1H), 10.82 (s, 1H), 13.65 (s, 1H).

Example 5

Preparation of (Z)-5-((5-fluoro-2-oxoindolin-3-ylidene)methyl)-N-(2-(4-(hydroxycarbamoyl)phenoxy)ethyl)-2,4-dimethyl-1H-pyrrole-3-carboxamide (Compound 8)

Step 5a. Methyl 4-(cyanomethoxy)benzoate (Compound 201)

To a solution of methyl 4-hydroxylbenzoate (5.0 g, 32.9 mmol) in DMF (50 mL) was added 2-Chloroacetonitrile (2.5 g, 32.9 mmol) and $K_2CO_3$ (13.6 g, 98.6 mmol). The mixture was stirred at 50° C. for 4 h. Water (100 ml) was added and resulting solid was filtered to give product 201 as a white solid (6.2 g, 98%). The solid was used in the next step without further purification. LCMS: 192 [M+1]$^+$.

Step 5b. Methyl 4-(2-aminoethoxy)benzoate (Compound 202)

A solution of compound 201 (1.5 g, 7.8 mmol) in THF (15 mL) was stirred at refluxing temperature under $N_2$ atmosphere. $BH_3 \cdot Me_2S$ (3.9 mL, 7.8 mmol) was added dropwise over 30 minutes. The solution was refluxed for 4 hours and then cooled to room temperature. 6N HCl (3 ml) was added and the mixture was refluxed for 0.5 hours and then cooled to 0° C. The reaction mixture was filtered and the filtrate was concentrated to give crude product 202 as a white solid (2.3 g). The crude product was used in the next step without further purification. LCMS: 196 [M+1]$^+$.

Step 5c. (Z)-Methyl 4-(2-(5-((5-fluoro-2-oxoindolin-3-ylidene)methyl)-2,4-dimethyl-1H-pyrrole-3-carboxamido) ethoxy)benzoate (Compound 203)

To a stirred solution of compound 109 (0.5 g, 1.67 mmol) in THF (150 mL) at 0° C. was added HOBt (0.34 g, 2.8 mmol), triethylamine (0.6 mL, 4.18 mmol), ECDI.HCl (0.48 g, 2.8 mmol) and compound 202 (0.6 g, 3.33 mmol) successively. The mixture was stirred overnight at room temperature, evaporated to remove solvent, diluted with water (50 mL), brine (50 mL) and saturated sodium bicarbonate solution (50 mL). The pH of solution was adjusted to 11~12 with 10M NaOH. The mixture was filtered, washed with water, dried to obtain crude yellow solid 203 (550 mg, 69%). LCMS: 478 [M+1]$^+$, $^1$H NMR (DMSO-$d_6$): δ 2.40 (s, 3H), 2.43 (s, 3H), 3.63 (m, 2H), 3.82 (s, 3H), 4.20 (t, 2H), 6.92 (m, 2H), 7.07 (d, 2H), 7.70 (m, 2H), 7.84 (s, 1H), 7.91 (d, 2H), 10.88 (s, 1H), 13.68 (s, 1H).

Step 5d. (z)-4-(2-(5-((5-Fluoro-2-oxoindolin-3-ylidene)methyl)-2,4-dimethyl-1H-pyrrole-3-carboxamido)ethoxy)benzoic Acid (Compound 8)

NaH (60%, 650 mg, 15.75 mmol) was added to the solution of hydroxylamine hydrochloride (750 mg, 10.5 mmol) in DMF (15 mL) portionwise at 0° C. After 0.5 h, the solution of compound 203 (500 mg, 1.05 mmol) in DMF (25 mL) was added to the above mixture. The mixture was stirred for 0.5 h at 0° C. and filtered. The solid was washed with DMF, and the filtrate was concentrated under reduced pressure to obtain a yellow solid that was purified to give product 8 as a yellow solid (65 mg, 17%). LCMS: 479 [M+1]+, $^1$H NMR (DMSO-$d_6$): δ 2.39 (s, 3H), 2.41 (s, 3H), 3.59 (m, 2H), 4.15 (t, J=5.7 Hz, 2H), 6.83 (m, 4H), 7.69 (m, 5H), 8.85 (s, 1H), 10.84 (s, 1H), 11.02 (s, 1H), 13.67 (s, 1H).

Example 6

Preparation of (Z)-5-((5-fluoro-2-oxoindolin-3-ylidene)methyl)-N-(6-(hydroxy(methyl)amino)-6-oxohexyl)-2,4-dimethyl-1H-pyrrole-3-carboxamide (Compound 9)

NaH (60%, 700 mg, 17.55 mmol) was added to a solution of N-methyl hydroxylamine hydrochloride (1 g, 11.7 mmol) in DMF (15 mL) portionwise at 0° C. After 0.5 h, a solution of compound 110-4 (0.5 g, 1.15 mmol) in DMF (25 mL) was added. The mixture was stirred for 15 min at 0° C., filtered and washed with DMF. The filtrate was concentrated under reduced pressure to obtain crude yellow solid that was purified to give desired product 9 as a yellow solid (150 mg, 35%). LCMS: 443 [M+1]+, $^1$H NMR (DMSO-$d_6$): δ 1.28 (m, 2H), 1.47 (m, 4H), 2.31 (m, 2H), 2.38 (s, 3H), 2.40 (s, 3H), 3.06 (s, 3H), 3.15 (m, 2H), 6.83 (m, 2H), 7.60 (t, J=5.85 Hz, 1H), 7.69 (s, 1H), 7.73 (m, 1H), 9.72 (s, 1H), 10.86 (s, 1H), 13.65 (s, 1H).

Example 7

Preparation of N-(2-aminophenyl)-5-((Z)-(5-fluoro-2-oxoindolin-3-ylidene)methyl)-2,4-dimethyl-1H-pyrrole-3-carboxamide (Compound 10)

To a stirred solution of compound 109 (0.2 g, 0.67 mmol) in DMF (30 mL) at 0° C. was added HOBt (0.136 g, 1.0 mmol), triethylamine (0.24 mL, 1.67 mmol), ECDI.HCl (0.192 g, 1.0 mmol) and benzene-1,2-diamine (0.2 g, 2.0 mmol) successively. The mixture was stirred for 72 h at room temperature, diluted with water (20 mL), brine (20 mL) and saturated aqueous sodium bicarbonate (20 mL). The pH of solution was adjusted to 11~12 with 10M NaOH. The mixture was filtered, washed with water, dried to obtain the product 10 as a yellow solid (0.13 g, 50.03%). LCMS: 391 [M+1]+, $^1$H NMR (DMSO-$d_6$): δ 4.83 (s, 2H), 6.58 (t, J=7.2 Hz, 1H), 6.78 (d, 1H), 6.84 (m, 1H), 6.92 (t, J=7.8 Hz, 2H), 7.25 (d, 1H), 7.74 (m, 2H), 9.00 (s, 1H), 10.90 (d, 1H), 13.75 (s, 1H), $^1$H NMR (DMSO-D$_2$O) δ 2.41 (s, 3H), 2.44 (s, 3H), 6.62 (t, J=7.4 Hz, 1H), 6.78 (d, 1H), 6.89 (m, 1H), 6.95 (m, 2H), 7.19 (d, 1H), 7.67 (m, 2H).

Example 8

Preparation of 5-((Z)-(5-fluoro-2-oxoindolin-3-ylidene)methyl)-N-(2-(4-((E)-3-(hydroxyamino)-3-oxoprop-1-enyl)phenoxy)ethyl)-2,4-dimethyl-1H-pyrrole-3-carboxamide (Compound 14)

Step 8a. (E)-Methyl 3-(4-(2-bromoethoxy)phenyl)acrylate (Compound 301)

To a solution of (E)-methyl 3-(4-hydroxylphenyl)acrylate (2.0 g, 11.24 mmol) in DMF (2.5 mL) was added 1,2-Dibromoethane (40 ml), K$_2$CO$_3$ (4.66 g, 33.7 mmol). The mixture was stirred at 90° C. for 6 hour and filtered. The filtrate was evaporated to give product 301 as a white solid (3.05 g, 95.2%). LCMS: 286 [M+1]+.

Step 8b. (E)-Methyl 3-(4-(2-(1,3-dioxoisoindolin-2-yl)ethoxy)phenyl)acrylate (Compound 302)

A mixture of compound 301 (1.5 g, 5.26 mmol), potassium phthalimide (1.07 g, 5.79 mmol) in DMF (20 mL) was stirred for 4 hours at 100° C. The reaction was cooled and the resulting solid was filtered. The filtrate was concentrated under reduced pressure to give product 302 as a white solid (1.75 g, 95.1%). LCMS: 352 [M+1]+.

Step 8c. (E)-Methyl 3-(4-(2-aminoethoxy)phenyl)acrylate (Compound 303)

To a suspension of compound 302 (1.85 g, 5.26 mmol) in EtOH (25 ml) was added hydrazine hydrate (0.4 mL, 7.89 mmol). The resulting mixture was refluxed for 10 hours and filtered. The filtrate concentrated to give desired product 303 (1.1 g, 95%). LCMS: 222 [M+1]+.

Step 8d. (E)-Methyl 3-(4-(2-(5-((Z)-(5-fluoro-2-oxoindolin-3-ylidene)methyl)-2,4-dimethyl-1H-pyrrole-3-carboxamido)ethoxy)phenyl)acrylate (Compound 304)

To a stirred solution of compound 109 (0.5 g, 1.67 mmol) in DMF (40 mL) at 0° C. was added HOBt (0.34 g, 2.5 mmol), triethylamine (0.94 mL, 6.68 mmol), ECDI.HCl (0.48 g, 2.5 mmol) and compound 303 (0.44 g, 2.0 mmol) successively. The mixture was stirred overnight at room temperature, evaporated, diluted with water (50 mL), brine (50 mL) and saturated aqueous sodium bicarbonate (50 mL). The pH of solution was adjusted to 11~12 with 10M NaOH. The mixture was filtered, washed with water, dried to obtain desired product 304 as a yellow solid (630 mg, 75%). LCMS: 504 [M+1]+, $^1$H NMR (DMSO-$d_6$): δ 2.39 (s, 3H), 2.41 (s, 3H), 3.59 (m, 2H), 3.69 (s, 3H), 4.15 (t, J=4.5 Hz, 2H), 6.45 (d, 1H), 6.94 (m, 4H), 7.65 (m, 6H), 10.87 (s, 1H), 13.66 (s, 1H).

Step 8e. 5-((z)-(5-Fluoro-2-oxoindolin-3-ylidene)methyl)-N-(2-(4-((E)-3-(hydroxyamino)-3-oxoprop-1-enyl)phenoxy)ethyl)-2,4-dimethyl-1H-pyrrole-3-carboxamide (Compound 14)

NaH (60%, 894 mg, 22.3 mmol) was added to the solution of hydroxylamine hydrochloride (1.035 g, 14.9 mmol) in DMF (15 mL) portionwise at 0° C. After 0.5 h, the solution of compound 304 (750 mg, 1.49 mmol) in DMSO (40 mL) was added to the above mixture. The mixture was stirred for 15 minutes at 0° C. and filtered, washed with DMF, and the filtrate was concentrated under reduced pressure. The residue was purified to give title compound 14 as a yellow solid (25 mg, 3.3%). LCMS: 505 [M+1]+, $^1$H NMR (DMSO-$d_6$): δ 2.38 (s, 3H), 2.41 (s, 3H), 3.58 (m, 2H), 4.13 (t, J=5.4 Hz, 2H), 6.27 (d, 1H), 6.98 (m, 4H), 7.41 (d, 1H), 7.48 (d, 2H), 7.69 (s, 1H), 7.75 (m, 1H), 7.81 (m, 1H), 10.87 (s, 1H), 13.66 (s, 1H).

Example 9

Preparation of (Z)-5-((5-fluoro-2-oxoindolin-3-ylidene)methyl)-N-(7-(hydroxyl-amino)-7-oxoheptyl)-2,4-dimethyl-1H-pyrrole-3-carboxamide (Compound 15)

Step 9a. (Z)-Methyl 7-(5-(((5-fluoro-2-oxoindolin-3-ylidene)methyl)-2,4-dimethyl-1H-pyrrole-3-carboxamido)heptanoate (Compound 110-15)

To a stirred solution of compound 109 (220.0 mg, 0.73 mmol) in DMF (15 mL) at room temperature was added HOBt (148.6 mg, 1.1 mmol), triethylamine (0.21 mL, 1.46 mmol), ECDI.HCl (210.2 mg, 1.1 mmol) and methyl 7-aminoheptanoate hydrochloride (157.1 mg, 0.8 mmol) successively. The mixture was stirred for 24 h at room temperature and was then diluted with water (20 mL), brine (20 mL) and saturated bicarbonate solution (20 mL). The pH of the mixture was adjusted to 11~12 with 10 N NaOH. The mixture was filtered and the solid was washed with water, dried to obtain a crude product 110-15 as a yellow solid (0.3 g, 93.2%). LCMS: 442 [M+1]$^+$; $^1$H NMR (DMSO-d$_6$): δ 1.31 (m, 4H), 1.50 (m, 4H), 2.31 (t, J=7.35 Hz, 2H), 2.40 (s, 3H), 2.42 (s, 3H), 3.19 (m, 2H), 3.59 (s, 3H), 6.87 (m, 2H), 7.71 (m, 3H), 10.91 (s, 1H), 13.67 (s, 1H).

Step 9b. (Z)-5-((5-Fluoro-2-oxoindolin-3-ylidene)methyl)-N-(7-(hydroxyamino)-7-oxoheptyl)-2,4-dimethyl-1H-pyrrole-3-carboxamide (Compound 15)

The NaH (60%, 140 mg, 3.5 mmol g) was added to the solution of hydroxylamine hydrochloride (160 mg, 2.3 mmol) in DMF (3 mL) at ice bath temperature and stirred for 0.5 h. To the mixture was added the solution of 110-15 (100.0 mg, 0.23 mmol) in DMSO (5 mL). The resulting mixture was stirred for 0.5 h at 0° C. and filtered. The solid was washed with DMF. The combined filtrate was concentrated under reduced pressure to give a residue which was purified by preparative HPLC to afford the title compound as a yellow solid (63 mg, 63%). m.p. 221° C. (decomp.) LCMS: 443 [M+1]$^+$; $^1$H NMR (DMSO-d$_6$): δ 1.29 (m, 4H) 1.48 (m, 4H), 1.93 (t, J=7.2 Hz, 2H), 2.38 (s, 3H), 2.40 (s, 3H), 3.19 (m, 2H), 6.87 (m, 2H), 7.69 (m, 3H), 10.31 (s, 1H), 10.87 (s, 1H), 13.65 (s, 1H).

Example 10

Preparation of (Z)-5-((5-fluoro-2-oxoindolin-3-ylidene)methyl)-N-(8-(hydroxylamino)-8-oxooctyl)-2,4-dimethyl-1H-pyrrole-3-Carboxamide (Compound 16)

Step 10a. (Z)-Methyl 8-(5-((5-fluoro-2-oxoindolin-3-ylidene)methyl)-2,4-dimethyl-1H-pyrrole-3-carboxamido)octanoate (Compound 110-16)

To a stirred solution of compound 109 (500 mg, 1.67 mmol) in DMF (40 mL) at room temperature was added HOBt (337.8 mg, 2.5 mmol), triethylamine (0.94 mL, 6.68 mmol), ECDI.HCl (477.8 mg, 2.5 mmol) and methyl 8-aminooctanoate hydrochloride (385.3 mg, 1.84 mmol) successively. The mixture was stirred for 24 h at room temperature and diluted with water (20 mL), brine (20 mL) and saturated sodium bicarbonate solution (20 mL). The pH of solution was adjusted to 11~12 with 10 N NaOH. The mixture was filtered and the solid was washed with water, dried to obtain a crude product 110-16 as a yellow solid (0.62 g, 86.1%). LCMS: 456 [M+1]+$^1$H NMR (DMSO-d$_6$): δ 1.28 (m, 6H), 1.50 (m, 4H), 2.28 (t, J=7.35 Hz, 2H), 2.38 (s, 3H), 2.40 (s, 3H), 3.20 (m, 2H), 3.56 (s, 3H), 6.84 (m, 2H), 7.69 (m, 3H), 10.87 (s, 1H), 13.65 (s, 1H).

Step 10b. (Z)-5-((5-Fluoro-2-oxoindolin-3-ylidene)methyl)-N-(8-(hydroxyamino)-8-oxooctyl)-2,4-dimethyl-1H-pyrrole-3-carboxamide (Compound 16)

The NaH (60%, 736 mg, 18.4 mmol) was added to the solution of hydroxylamine hydrochloride (855 mg, 12.3 mmol) in DMF (15 mL) at ice bath temperature and stirred for 0.5 h. To the mixture was added the solution of compound 110-16 (560 mg, 1.23 mmol) in DMSO (25 mL). The resulting mixture was stirred for 0.5 hours at 0° C. and filtered. The solid was washed with DMF. The combined filtrate was concentrated under reduced pressure to give a residue which was purified by preparative HPLC to afford product 16 as a yellow solid (40 mg, 7%). m.p. 213.7° C. (decomp.). LCMS: 457 [M+1]$^+$; $^1$H NMR (DMSO-d$_6$): δ 1.27 (m, 6H) 1.47 (m, 4H), 1.92 (t, J=6.9 Hz, 2H), 2.38 (s, 3H), 2.40 (s, 3H), 3.18 (m, 2H), 6.87 (m, 2H), 7.70 (m, 3H), 8.66 (s, 1H), 10.32 (s, 1H), 10.88 (s, 1H), 13.66 (s, 1H).

Example 11

Preparation of (Z)-N-(6-(acetoxyamino)-6-oxohexyl)-5-((5-fluoro-2-oxoindolin-3-ylidene)methyl)-2,4-dimethyl-1H-pyrrole-3-carboxamide (Compound 17)

Ac$_2$O (1.5 ml) was added to a solution of compound 4 (120 mg, 0.28 mmol) in AcOH (15 mL). The solution was stirred at room temperature for 4 hours. The mixture was adjusted to pH 7~8 with saturated aqueous NaHCO$_3$. The resulting solid was collected by filtration. The residue was washed with water three times, dried to give desired product 17 as a yellow solid (100 mg, 76%). LCMS: 471 [M+1], $^1$H NMR (DMSO-d$_6$): δ 1.32 (m, 2H), 1.53 (m, 4H), 2.12 (m, 5H), 2.39 (s, 3H), 2.41 (s, 3H), 3.20 (m, 2H), 6.85 (m, 2H), 7.581 (m, 1H), 7.69 (m, 2H), 10.84 (s, 1H), 11.52 (s, 1H), 13.65 (s, 1H).

Example 12

Preparation of (Z)-5-((5-fluoro-2-oxoindolin-3-ylidene)methyl)-N-(6-(isobutyryloxyamino)-6-oxohexyl)-2,4-dimethyl-1H-pyrrole-3-carboxamide (compound 18)

Isobutyric anhydride (7 mL, 42.2 mmol) was added to a solution of compound 4 (500 mg, 1.17 mmol) in AcOH (70 mL). The solution was stirred at room temperature for 4 hours and the mixture was adjusted to pH 7~8 with saturated aqueous NaHCO$_3$. The resulting solid was collected by filtration, washed with water for three times, dried and purified by preparative .HPLC to give product 18 as a yellow solid (35 mg, 6%). LCMS: 499 [M+1]$^+$, $^1$H NMR (DMSO-d$_6$): δ 1.12 (s, 3H), 1.14 (s, 3H), 1.34 (m, 2H), 1.55 (m, 4H), 2.11 (t, J=6.9 Hz, 2H), 2.39 (s, 3H), 2.41 (s, 3H), 2.69 (m, 1H), 3.18 (m, 2H), 6.83 (m, 2H), 7.63 (m, 3H), 10.88 (s, 1H), 11.54 (s, 1H), 13.66 (s, 1H).

Example 13

Preparation of (Z)-N-(6-(benzoyloxyamino)-6-oxohexyl)-5-((5-fluoro-2-oxoindolin-3-ylidene)methyl)-2,4-dimethyl-1H-pyrrole-3-carboxamide (Compound 19)

Benzoic anhydride (200 mg, 0.88 mmol) was added to a solution of compound 4 (200 mg, 0.47 mmol) in AcOH (40 mL). The solution was stirred at room temperature for 4 hours and then adjusted to pH 7~8 with saturated aqueous $NaHCO_3$. The resulting solid was collected by filtration, washed with water for three times, dried and purified by preparative HPLC to give product 19 as a yellow solid (40 mg, 16%). LCMS: 533 [M+1]$^+$, $^1$H NMR (DMSO-d$_6$): δ 1.35 (m, 2H), 1.53 (m, 4H), 2.12 (t, J=7.05 Hz, 2H), 2.40 (s, 3H), 2.41 (s, 3H), 3.20 (m, 2H), 6.85 (m, 2H), 7.57 (m, 1H), 7.70 (m, 3H), 7.99 (s, 1H), 8.01 (s, 1H), 10.88 (s, 1H), 11.88 (s, 1H), 13.66 (s, 1H).

Example 14

Preparation of (Z)-5-((5-fluoro-2-oxoindolin-3-ylidene)methyl)-2,4-dimethyl-N-(6-oxo-6-(propionyloxyamino)hexyl)-1H-pyrrole-3-carboxamide (Compound 20)

Propionic anhydride (7 mL, 54.4 mmol) was added to a solution of compound 4 (500 mg, 1.17 mmol) in AcOH (70 mL). The solution was stirred at room temperature for 4 hours and the mixture was adjusted to pH 7~8 with saturated $NaHCO_3$. The mixture was filtered, washed with water for three times, dried and purified by preparative HPLC to give product 20 as a yellow solid (180 mg, 32%). LCMS: 485 [M+1]$^+$, $^1$H NMR (DMSO-d$_6$): δ 1.06 (t, J=7.8 Hz, 3H), 1.31 (m, 2H), 1.52 (m, 4H), 2.11 (t, J=7.35 Hz, 2H), 2.38 (s, 3H), 2.40 (s, 3H), 2.44 (m, 2H), 3.17 (m, 2H), 6.82 (m, 2H), 7.66 (m, 3H), 10.84 (s, 1H), 11.51 (s, 1H), 13.64 (s, 1H).

Example 15

Preparation of (Z)-N-(6-(cyclohexanecarbonyloxyamino)-6-oxohexyl)-5-((5-fluoro-2-oxoindolin-3-ylidene)methyl)-2,4-dimethyl-1H-pyrrole-3-carboxamide (Compound 21)

Cyclohexanecarboxylic anhydride (5 mL) and cyclohexanecarboxylic acid (150 mg, 1.17 mmol) was added to a solution of compound 4 (500 mg, 1.17 mmol) in THF (120 ml) and DMF (5 mL). The solution was stirred at room temperature for 4 h. THF was removed in vacuo, and then water (100 mL) was added. The mixture was adjusted to pH 78 with saturated aqueous $NaHCO_3$. The resulting solid was collected by filtration, washed with water for three times, dried and purified by preparative HPLC to give product 21 as a yellow solid (100 mg, 13%). LCMS: 539 [M+1]$^+$, $^1$H NMR (DMSO-d$_6$): δ 1.32 (m, 7H), 1.53 (m, 5H), 1.66 (m, 2H), 1.85 (m, 2H), 2.11 (t, J=6.45 Hz, 2H), 2.39 (s, 3H), 2.41 (s, 3H), 3.20 (m, 2H), 6.85 (m, 2H), 7.71 (m, 3H), 10.89 (s, 1H), 11.54 (s, 1H), 13.67 (s, 1H).

Example 16

Preparation of (Z)-N-(7-(acetoxyamino)-7-oxoheptyl)-5-((5-fluoro-2-oxoindolin-3-ylidene)methyl)-2,4-dimethyl-1H-pyrrole-3-carboxamide (Compound 28)

Ac$_2$O (2 ml) was added to a solution of compound 15 (140 mg, 0.32 mmol) in 20 ml AcOH. The solution was stirred at room temperature for 4 h. Saturated $NaHCO_3$ was added slowly to adjust PH to 7~8. The solid was collected by filtration, washed with water for three times, dried to give crude product which was purified by prep-HPLC to give product 28 (95 mg, 62%). LCMS: 485 [M+1]$^+$, $^1$H NMR (DMSO-d$_6$) δ 1.30 (m, 4H), 1.51 (m, 4H), 2.07 (m, 5H), 2.38 (s, 3H), 2.40 (s, 3H), 3.19 (m, 2H), 6.84 (m, 2H), 7.62 (t, J=6.0 Hz, 1H), 7.69 (s, 1H), 7.75 (m, 1H), 10.87 (s, 1H), 11.54 (s, 1H), 13.65 (s, 1H).

Example 17

Preparation of ethyl (Z)-N-(8-(acetoxyamino)-8-oxooctyl)-5-((5-fluoro-2-oxoindolin-3-ylidene)methyl)-2,4-dimethyl-1H-pyrrole-3-carboxamide (Compound 29)

Ac$_2$O (3 ml) was added to a solution of compound 16 (228 mg, 0.5 mmol) in 30 ml AcOH. The solution was stirred at room temperature for 4 h. Saturated $NaHCO_3$ was added slowly to adjust PH to 7~8. The solid was collected by filtration, washed with water for three times, dried to give crude product which was purified by prep-HPLC to give product 29 (50 mg, 20%). LCMS: 499 [M+1]$^+$, $^1$H NMR (DMSO-d$_6$) δ 1.29 (m, 6H), 1.49 (m, 4H), 2.07 (t, 2H), 2.12 (s, 3H), 2.38 (s, 3H), 2.40 (s, 3H), 3.20 (m, 2H), 6.85 (m, 2H), 7.63 (t, J=5.6 Hz, 1H), 7.70 (s, 1H), 7.76 (m, 1H), 10.88 (s, 1H), 11.53 (s, 1H), 13.65 (s, 1H).

Biological Assays:

As stated hereinbefore the derivatives defined in the present invention possess anti-proliferation activity. These properties may be assessed, for example, using one or more of the procedures set out below:

(a) An In Vitro Assay which—Determines the Ability of a Test Compound to Inhibit a Receptor Tyrosine Kinase.

The ability of compounds to inhibit receptor kinase (VEGFR2 and PDGFR-beta) activity was assayed using HTScan™ Receptor Kinase Assay Kits (Cell Signaling Technologies, Danvers, Mass.). VEGFR2 tyrosine kinase was produced using a baculovirus expression system from a construct containing a human VEGFR2 cDNA kinase domain (Asp805-Val1356) (GenBank accession No. AF035121) fragment amino-terminally fused to a GST-HIS6-Thrombin cleavage site. PDGFR-beta tyrosine kinase was produced using a baculovirus expression system from a construct containing a human PDGFR-beta c-DNA (GenBank Accession No. NM_002609) fragment (Arg561-Leu1106) amino-terminally fused to a GST-HIS6-Thrombin cleavage site. The proteins were purified by one-step affinity chromatography using glutathione-agarose. An anti-phosphotyrosine monoclonal antibody, P-Tyr-100, was used to detect phosphorylation of biotinylated substrate peptides (VEGFR2, Biotin-Gastrin Precursor (Tyr87); PDGFR-β, Biotinylated-FLT3 (Tyr589)). Enzymatic activity was tested in 60 mM HEPES, 5 mM MgCl2 5 mM MnCl2 200 μM ATP, 1.25 mM DTT, 3 μM Na3VO4, 1.5 mM peptide, and 50 ng EGF Receptor Kinase. Bound antibody was detected using the DELFIA system (PerkinElmer, Wellesley, Mass.) consisting of DELFIA® Europium-labeled Anti-mouse IgG (PerkinElmer, #AD0124), DELFIA® Enhancement Solution (PerkinElmer, #1244-105), and a DELFIA® Streptavidin coated, 96-well Plate (PerkinElmer, AAAND-0005). Fluorescence was measured on a WALLAC Victor 2 plate reader and reported as relative fluorescence units (RFU). Data were plotted using GraphPad Prism (v4.0a) and IC50's calculated using a sigmoidal dose response curve fitting algorithm.

Test compounds were dissolved in dimethylsulphoxide (DMSO) to give a 20 mM working stock concentration. Each assay was setup as follows: Added 100 μl of 10 mM ATP to 1.25 ml 6 mM substrate peptide. Diluted the mixture with dH$_2$0 to 2.5 ml to make 2×ATP/substrate cocktail ([ATP]=400 mM, [substrate]=3 mM). Immediately transfer enzyme from −80° C. to ice. Allowed enzyme to thaw on ice. Microcentrifuged briefly at 4° C. to bring liquid to the bottom of the vial. Returned immediately to ice. Added 10 μl of DTT (1.25 mM) to 2.5 ml of 4×HTScan™ Tyrosine Kinase Buffer (240 mM HEPES pH 7.5, 20 mM MgCl$_2$, 20 mM MnCl, 12 mM NaVO$_3$) to make DTT/Kinase buffer. Transfer 1.25 ml of DTT/Kinase buffer to enzyme tube to make 4× reaction cocktail ([enzyme]=4 ng/μL in 4× reaction cocktail). Incubated 12.5 μl of the 4× reaction cocktail with 12.5 μl/well of prediluted compound of interest (usually around 10 μM) for 5 minutes at room temperature. Added 25 μl of 2×ATP/substrate cocktail to 25 μg/well preincubated reaction cocktail/compound. Incubated reaction plate at room temperature for 30 minutes. Added 50 μl/well Stop Buffer (50 mM EDTA, pH 8) to stop the reaction. Transferred 25 μl of each reaction and 75 μl dH$_2$O/well to a 96-well streptavidin-coated plate and incubated at room temperature for 60 minutes. Washed three times with 200 μl/well PBS/T (PBS, 0.05% Tween-20). Diluted primary antibody, Phospho-Tyrosine mAb (P-Tyr-100), 1:1000 in PBS/T with 1% bovine serum albumin (BSA). Added 100 μl/well primary antibody. Incubated at room temperature for 60 minutes. Washed three times with 200 μl/well PBS/T. Diluted Europium labeled anti-mouse IgG 1:500 in PBS/T with 1% BSA. Added 100 μl/well diluted antibody. Incubated at room temperature for 30 minutes. Washed five times with 200 μl/well PBS/T. Added 100 μl/well DELFIA® Enhancement Solution. Incubated at room temperature for 5 minutes. Detected 615 nm fluorescence emission with appropriate Time-Resolved Plate Reader.

(b) An In Vitro Assay which Determines the Ability of a Test Compound to Inhibit HDAC Enzymatic Activity.

HDAC inhibitors were screened using an HDAC fluorimetric assay kit (AK-500, Biomol, Plymouth Meeting, Pa.). Test compounds were dissolved in dimethylsulphoxide (DMSO) to give a 20 mM working stock concentration. Fluorescence was measured on a WALLAC Victor 2 plate reader and reported as relative fluorescence units (RFU). Data were plotted using GraphPad Prism (v4.0a) and IC50's calculated using a sigmoidal dose response curve fitting algorithm. Each assay was setup as follows: Defrosted all kit components and kept on ice until use. Diluted HeLa nuclear extract 1:29 in Assay Buffer (50 mM Tris/Cl, pH 8.0, 137 mM NaCl, 2.7 mM KCl, 1 mM MgCl2). Prepared dilutions of Trichostatin A (TSA, positive control) and tested compounds in assay buffer (5× of final concentration). Diluted Fluor de Lys™ Substrate in assay buffer to 100 uM (50 fold=2× final). Diluted Fluor de Lys™ developer concentrate 20-fold (e.g. 50 μl plus 950 μl Assay Buffer) in cold assay buffer. Second, diluted the 0.2 mM Trichostatin A 100-fold in the 1× Developer (e.g. 10 μl in 1 ml; final Trichostatin A concentration in the 1× Developer=2 μM; final concentration after addition to HDAC/Substrate reaction=1 μM). Added Assay buffer, diluted trichostatin A or test inhibitor to appropriate wells of the microtiter plate. Added diluted HeLa extract or other HDAC sample to all wells except for negative controls. Allowed diluted Fluor de Lys™ Substrate and the samples in the microtiter plate to equilibrate to assay temperature (e.g. 25 or 37° C. Initiated HDAC reactions by adding diluted substrate (25 μl) to each well and mixing thoroughly. Allowed HDAC reactions to proceed for 1 hour and then stopped them by addition of Fluor de Lys™ Developer (501). Incubated plate at room temperature (25° C.) for 10-15 min. Read samples in a microtiter-plate reading fluorimeter capable of excitation at a wavelength in the range 350-380 nm and detection of emitted light in the range 440-460 nm.

The following TABLE B lists compounds representative of the invention and their activity in HDAC, VEGFR2 and PDGFR assays. In these assays, the following grading was used: I≧10 μM, 10 μM>II>1 μM, 1 μM>III>0.1 μM, and IV≦0.1 μM for IC$_{50}$.

TABLE B

| Compound No. | HDAC | VEGFR2 | PDGFR |
|---|---|---|---|
| 2 | III | IV | III |
| 3 | II | IV | IV |
| 4 | III | IV | IV |
| 8 | III | | |
| 9 | I | IV | |
| 14 | III | IV | |
| 15 | IV | IV | III |
| 16 | IV | IV | III |

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by formula I:

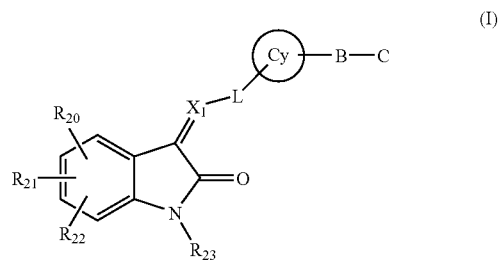

or a geometric isomer, enantiomer, diastereomer, racemate, pharmaceutically acceptable salt, or prodrug thereof, wherein $X_1$ is N, $CR_4$; where $R_4$ is hydrogen or aliphatic;

L is absent or NH;

Cy is aryl, substituted aryl, heteroaryl, or substituted heteroaryl;

G is O or S;

B is a linker;

C is selected from:

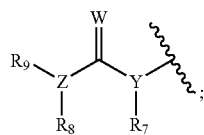

where W is O or S; Y is absent, N, or CH; Z is N or CH; $R_7$ and $R_9$ are independently hydrogen, OR' or aliphatic group, wherein R' is hydrogen, aliphatic, substituted aliphatic or acyl; provided that if $R_7$ and $R_9$ are both present, one of $R_7$ or $R_9$ must be OR' and if Y is absent, $R_9$ must be OR'; and $R_8$ is hydrogen, acyl, aliphatic, or substituted aliphatic;

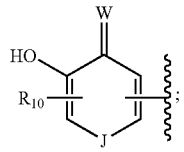

where W is O or S; J is O, NH or $NCH_3$; and $R_{10}$ is hydrogen or lower alkyl;

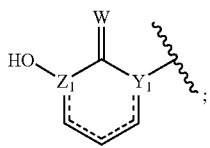

where W is O or S; $Y_1$ and $Z_1$ are independently N, C or CH; and

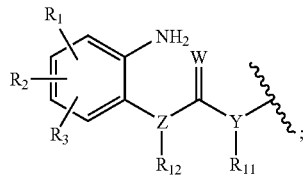

where Z, Y, and W are as previously defined; $R_{11}$ and $R_{12}$ are independently selected from hydrogen or aliphatic; $R_1$, $R_2$ and $R_3$ are independently selected from hydrogen, hydroxy, amino, halogen, alkoxy, substituted alkoxy, alkylamino, substituted alkylamino, dialkylamino, substituted dialkylamino, substituted or unsubstituted alkylthio, substituted or unsubstituted alkylsulfonyl, $CF_3$, CN, $N_3$, $NO_2$, sulfonyl, acyl, aliphatic, substituted aliphatic, aryl, substituted aryl, heteroaryl, substituted heteroaryl, heterocyclic, and substituted heterocyclic;

$R_{20}$, $R_{21}$ and $R_{22}$ are independently selected from $R_1$; and $R_{23}$ is hydrogen, acyl, aliphatic or substituted aliphatic.

2. A compound according to claim 1, wherein B is a direct bond or straight or branched, substituted or unsubstituted alkylene, substituted or unsubstituted alkenylene, substituted or unsubstituted alkynylene, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, or alkynylhereroaryl, which one or more methylenes can be interrupted or terminated by O, S, S(O), $SO_2$, $N(R_8)$, C(O), substituted or unsubstituted aryl, substituted or unsubstituted heteroaryl, substituted or unsubstituted heterocyclic; where $R_8$ is hydrogen, acyl, aliphatic or substituted aliphatic.

3. A compound according to claim 1 represented by formula (II):

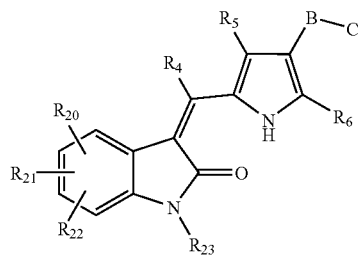

or a geometric isomer, enantiomer, diastereomer, racemate, pharmaceutically acceptable salt, or prodrug thereof, wherein $R_5$ and $R_6$ are independently selected from hydrogen, $CF_3$, aliphatic and substituted aliphatic; and $R_4$, $R_{20}$, $R_{21}$, $R_{22}$, $R_{23}$, G, B and C are as defined in claim 1.

4. A compound according to claim 1 represented by formula III:

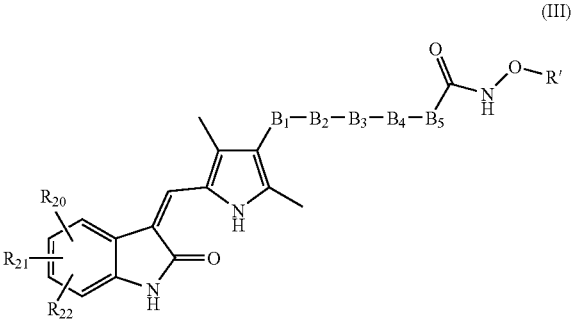

or a geometric isomer, enantiomer, diastereomer, racemate, pharmaceutically acceptable salt, or prodrug thereof, wherein $B_1$ is absent, O, S, SO, $SO_2$, aryl, heteroaryl, heterocyclic, $N(R_8)$, CO; $B_2$ is absent, $C_1$-$C_6$ alkyl, $C_2$-$C_6$ alkenyl, $C_2$-$C_6$ alkynyl, aryl, heteroaryl, heterocyclic, $N(R_8)$, CO, SO, or $SO_2$; $B_3$ is absent, O, $N(R_8)$, CO, $C_1$-$C_6$ alkyl, $C_2$-$C_6$ alkenyl, $C_2$-$C_6$ alkynyl, aryl, heteroaryl, or heterocyclic; $B_4$ is absent, O, S, SO, $SO_2$, $N(R_8)$, CO; $B_5$ is absent, $C_1$-$C_8$ alkyl, $C_2$-$C_8$ alkenyl, $C_2$-$C_8$ alkynyl, heterocyclic, heteroaryl or aryl; and R', $R_{20}$, $R_{21}$, and $R_{22}$ are as defined in claim 1.

5. A compound according to claim 1 represented by formula (IV):

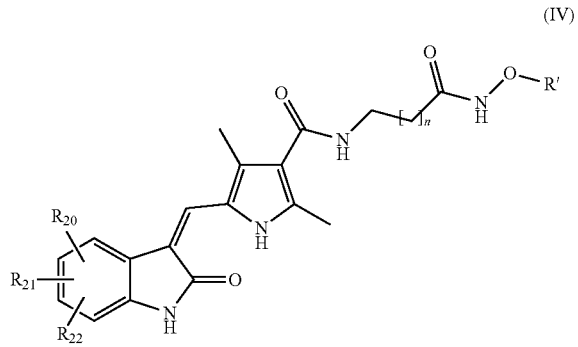

or a geometric isomer, enantiomer, diastereomer, racemate, pharmaceutically acceptable salt, or prodrug thereof, wherein n is 1-9; and R', $R_{20}$, $R_{21}$, and $R_{22}$ are as defined in claim 1.

6. A compound according to claim 1 represented by formula (V):

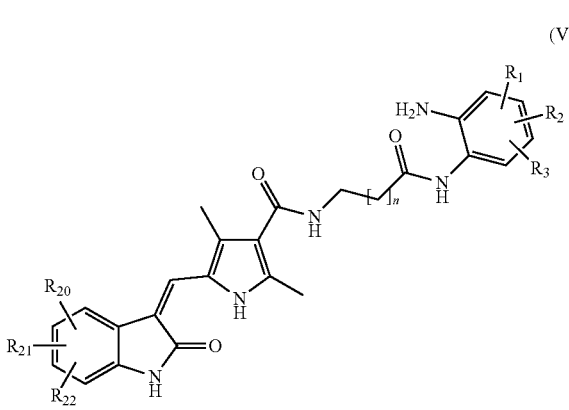

or a geometric isomer, enantiomer, diastereomer, racemate, pharmaceutically acceptable salt, or prodrug thereof, wherein n is 1-9; and $R_1$, $R_2$, $R_3$, $R_{20}$, $R_{21}$, and $R_{22}$ are as defined in claim 1.

7. A compound according to claim 1 represented by formula (VI):

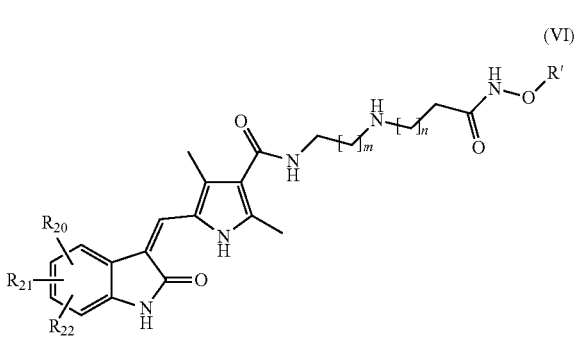

or a geometric isomer, enantiomer, diastereomer, racemate, pharmaceutically acceptable salt, or prodrug thereof, wherein n is 1-6; m is 1 or 2; R', $R_{20}$, $R_{21}$, and $R_{22}$ are as defined in claim 1.

8. A compound according to claim 1 represented by formula (VII):

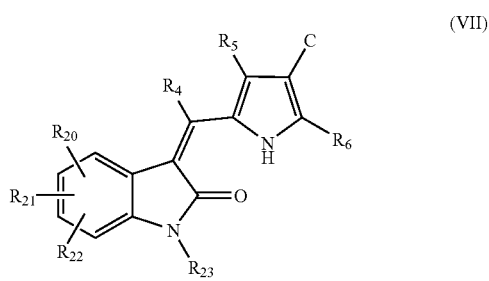

or a geometric isomer, enantiomer, diastereomer, racemate, pharmaceutically acceptable salt, or prodrug thereof, wherein C is —C(O)NHOR' or

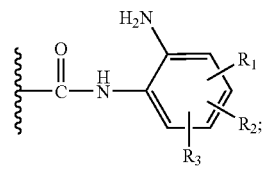

$R_5$ and $R_6$ are independently selected from hydrogen, $CF_3$, aliphatic and substituted aliphatic; and R', $R_4$, $R_5$, $R_6$, $R_{20}$, $R_{21}$, $R_{22}$, and $R_{23}$ are as defined in claim 1.

9. A compound according to claim 1 represented by formula (VIII):

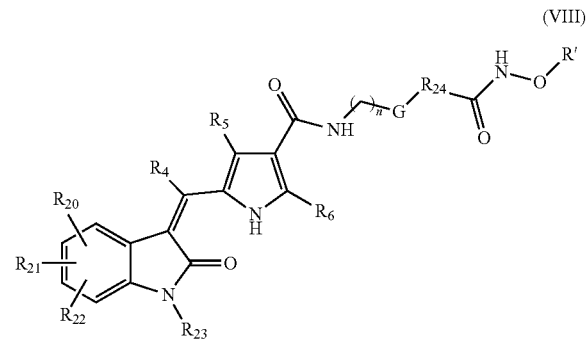

or a geometric isomer, enantiomer, diastereomer, racemate, pharmaceutically acceptable salt, or prodrug thereof, wherein n is 0-7; $R_{24}$ is absent or selected from alkylene, alkenylene, and alkynylene; n is 0-7; G is $Ar_1$, $X_2$-$Ar_1$ or $X_2$-alkyl -$Ar_1$, where $Ar_1$ is independently selected from Cy and $X_2$ is O, S or NH; $R_5$ and $R_6$ are independently selected from hydrogen, $CF_3$, aliphatic and substituted aliphatic; and Cy, R', $R_4$, $R_{20}$, $R_{21}$, $R_{22}$, and $R_{23}$ are as defined in claim 1.

10. A compound according to claim 1 selected from the compounds delineated in Table A or a geometric isomer, enantiomer, diastereomer, racemate, pharmaceutically acceptable salt, or prodrug thereof:

TABLE A

| Compound No. | Structure |
|---|---|
| 1 | (structure) |
| 2 | (structure) |
| 3 | (structure) |
| 4 | (structure) |
| 5 | (structure) |

TABLE A-continued
| Compound No. | Structure |
|---|---|
| 6 | 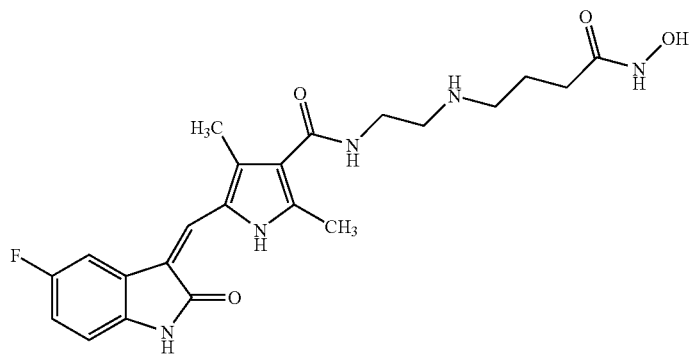 |
| 7 | 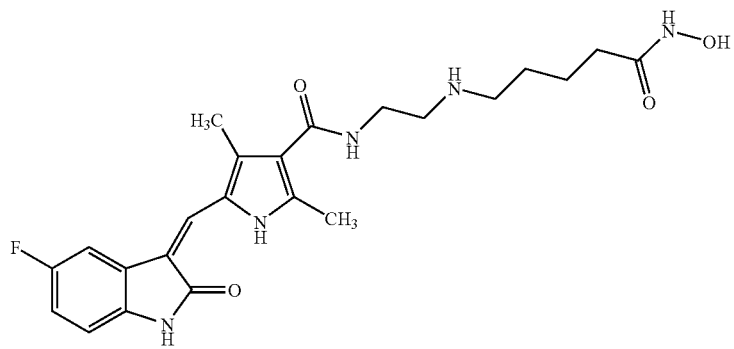 |
| 8 | 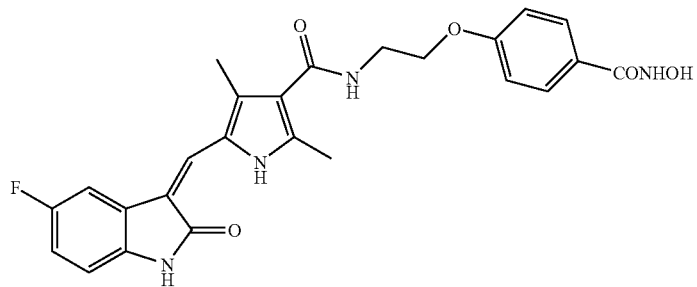 |
| 9 | 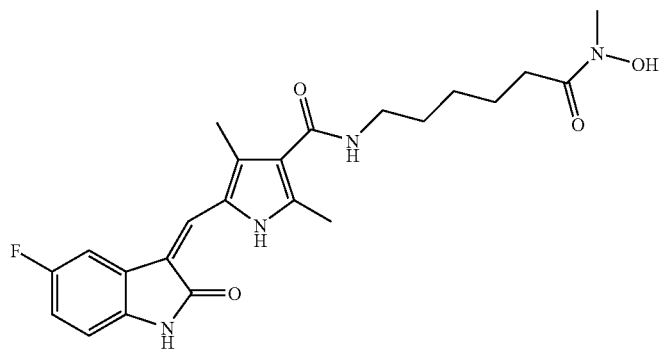 |

TABLE A-continued

| Compound No. | Structure |
|---|---|
| 10 | 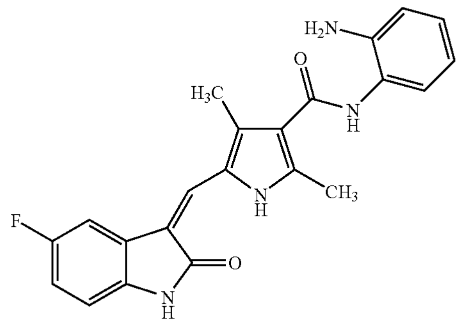 |
| 11 | 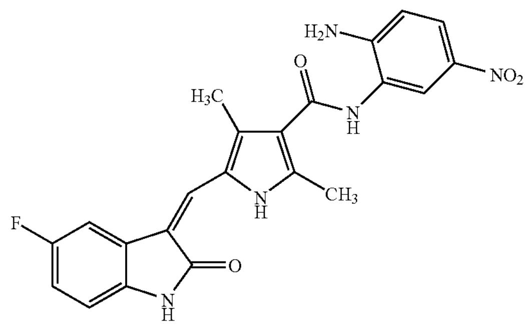 |
| 12 | 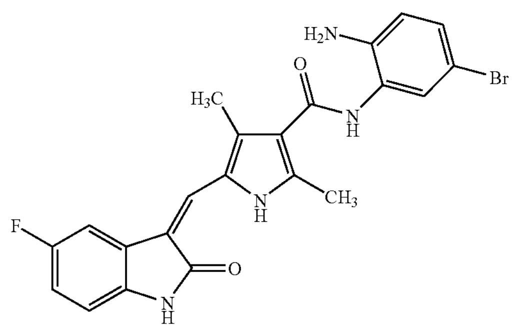 |
| 13 | 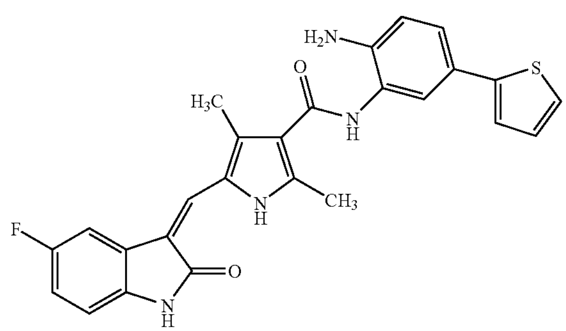 |
| 14 | 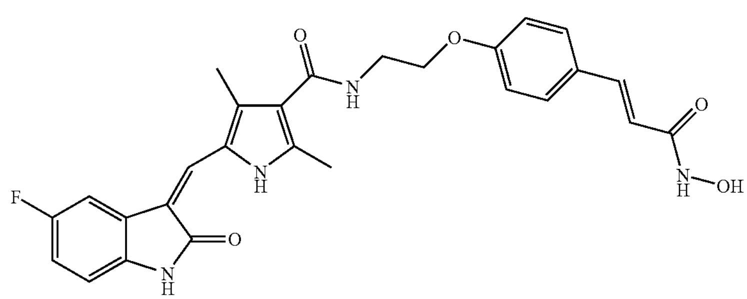 |

TABLE A-continued
| Compound No. | Structure |
|---|---|
| 15 | 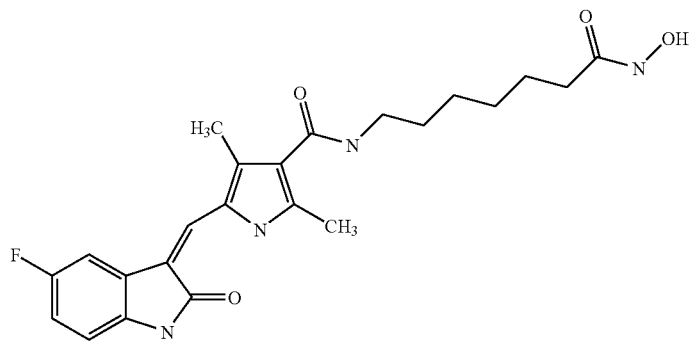 |
| 16 | 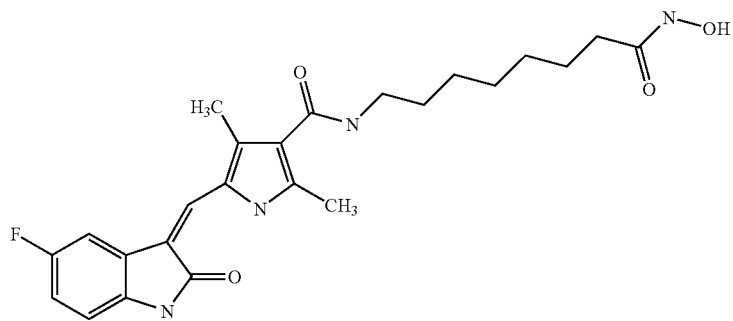 |
| 17 | 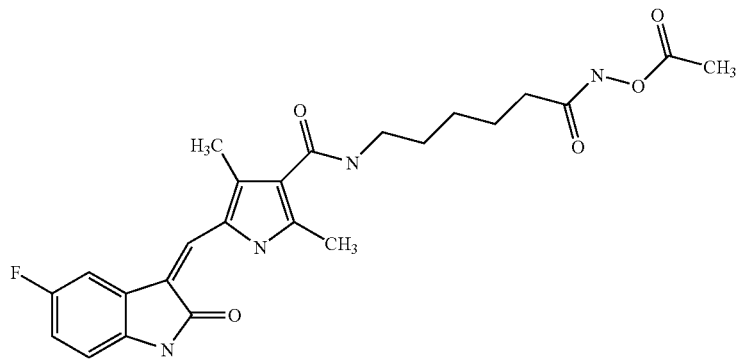 |
| 18 | 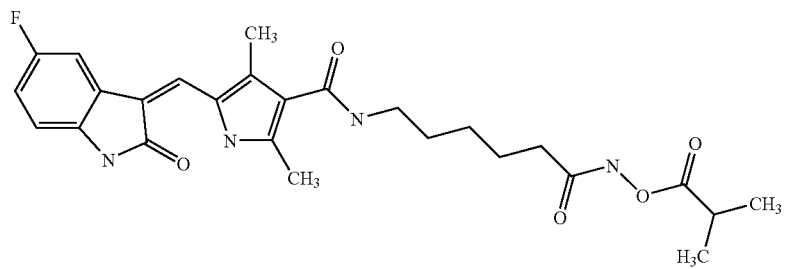 |

TABLE A-continued
| Compound No. | Structure |
|---|---|
| 19 | 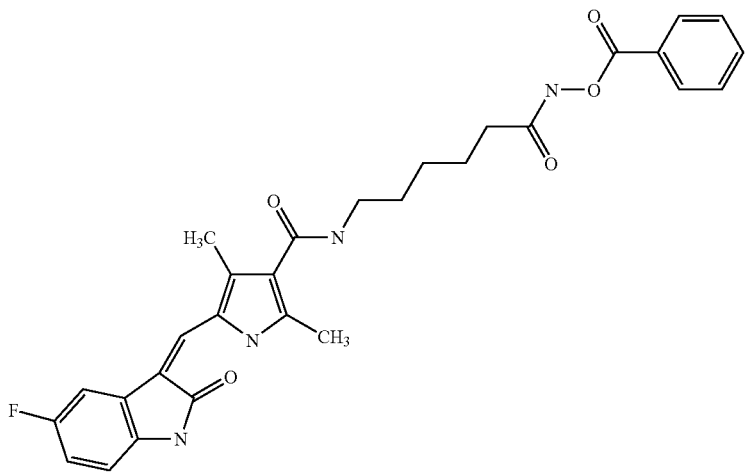 |
| 20 | 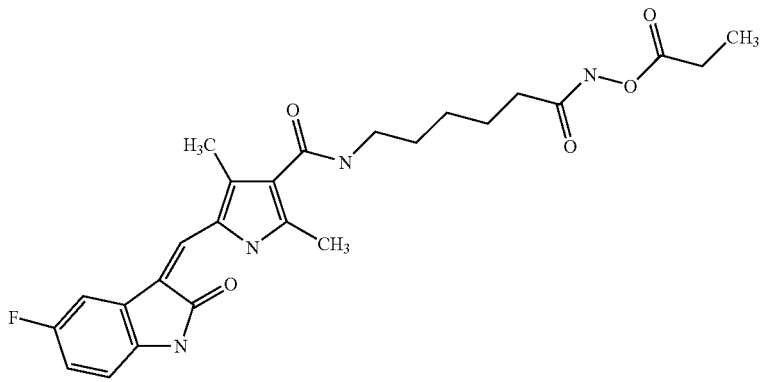 |
| 21 | 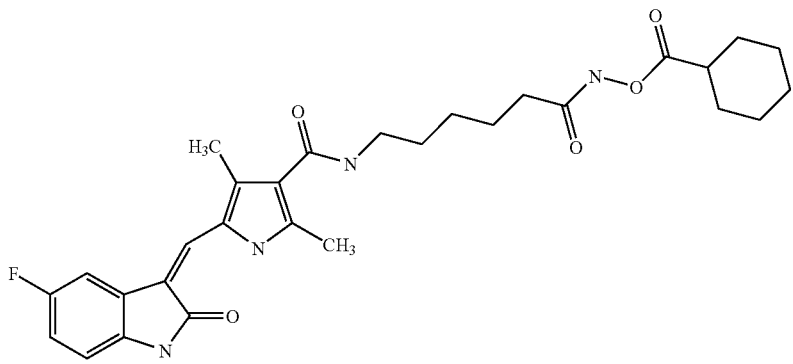 |
| 22 | 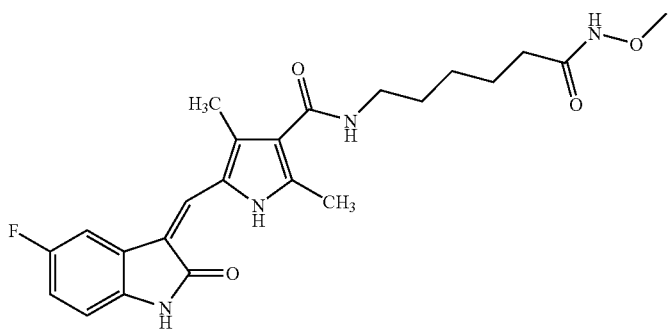 |

TABLE A-continued
| Compound No. | Structure |
|---|---|
| 23 | 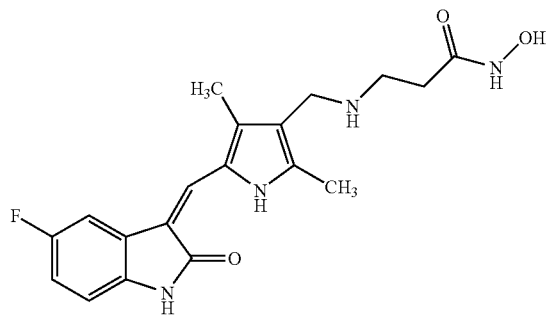 |
| 24 | 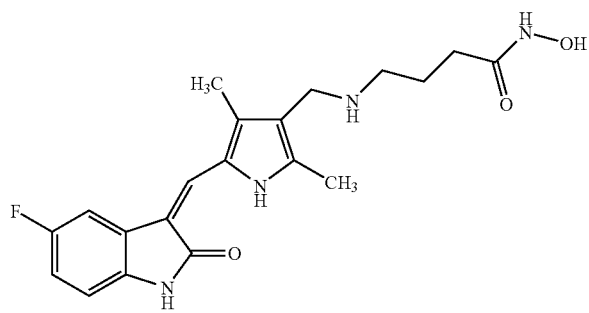 |
| 25 | 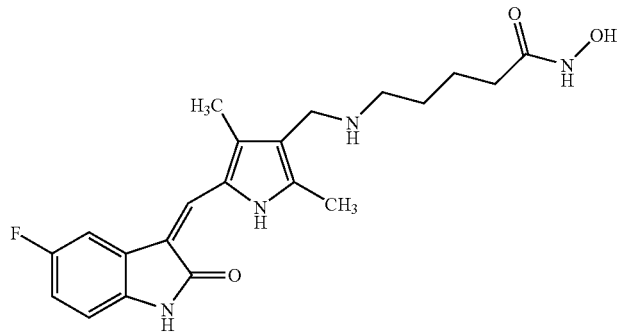 |
| 26 | 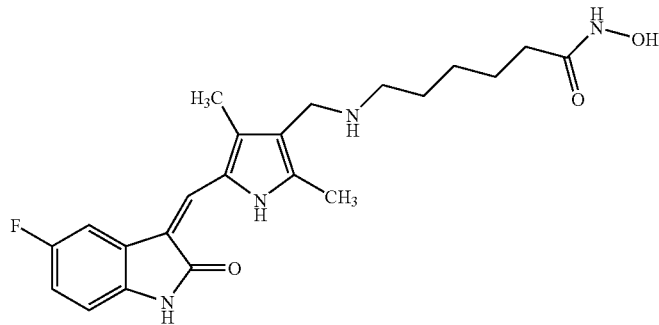 |

TABLE A-continued
| Compound No. | Structure |
| --- | --- |
| 27 | 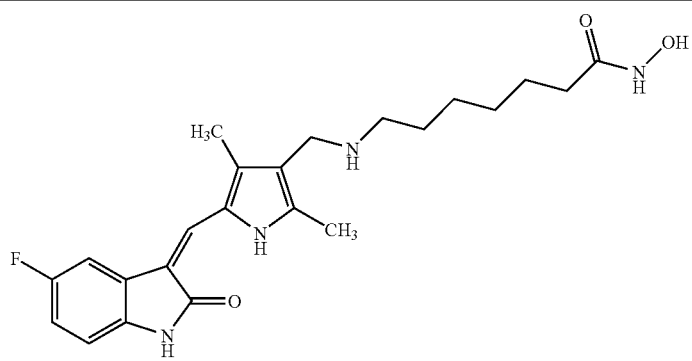 |
| 28 | 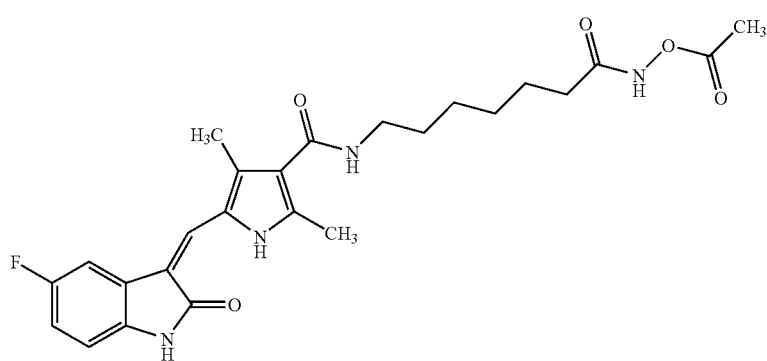 |
| 29 | 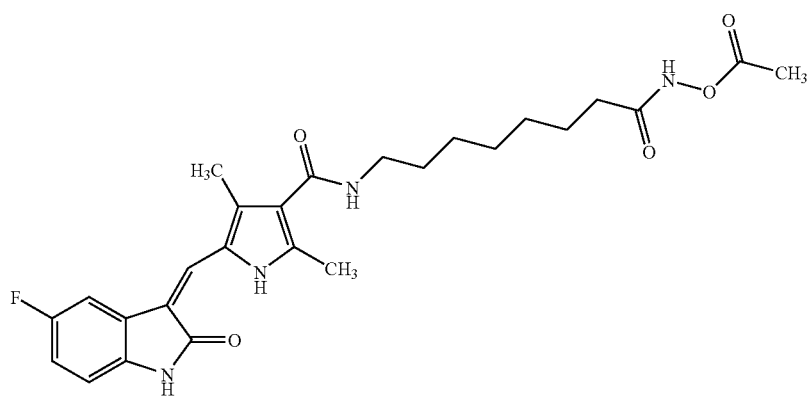 |
11. A pharmaceutical composition comprising as an active ingredient a compound of claim 1 and a pharmaceutical acceptable carrier.
* * * * *